(12) United States Patent
Martinez Hernandez Magro et al.

(10) Patent No.: US 10,950,346 B2
(45) Date of Patent: *Mar. 16, 2021

(54) UTILIZING ARTIFICIAL INTELLIGENCE FOR DATA EXTRACTION

(71) Applicant: International Business Machines Corporation, Armonk, NY (US)

(72) Inventors: Agueda Martinez Hernandez Magro, Zapopan (MX); Herbert Barrientos Carvajal, Filderstadt-Bonlanden (DE)

(73) Assignee: International Business Machines Corporation, Armonk, NY (US)

( * ) Notice: Subject to any disclaimer, the term of this patent is extended or adjusted under 35 U.S.C. 154(b) by 824 days.

This patent is subject to a terminal disclaimer.

(21) Appl. No.: 15/581,641

(22) Filed: Apr. 28, 2017

(65) Prior Publication Data

US 2018/0314955 A1 Nov. 1, 2018

(51) Int. Cl.
*G16H 50/20* (2018.01)
*G06N 5/04* (2006.01)
(Continued)

(52) U.S. Cl.
CPC ............. *G16H 50/20* (2018.01); *G06N 5/022* (2013.01); *G06N 5/045* (2013.01); *G16H 50/70* (2018.01); *G16H 70/60* (2018.01)

(58) Field of Classification Search
CPC ........ G16H 50/20; G16H 70/60; G16H 50/70; G06N 5/022; G06N 5/045
See application file for complete search history.

(56) References Cited

U.S. PATENT DOCUMENTS

| 4,945,476 A | 7/1990 | Bodick et al. |
| 6,212,528 B1 | 4/2001 | Brophy et al. |

(Continued)

OTHER PUBLICATIONS

Longxiang Shi, Shijian Li, Xiaoran Yang, Jiaheng Qi, Gang Pan, and Binbin Zhou, "Semantic Health Knowledge Graph: Semantic Integration of Heterogeneous Medical Knowledge and Services", Feb. 12, 2017, Hindawi BioMed Research International, vol. 2017, Article ID 2858423, pp. 1-12. (Year: 2017).*

(Continued)

*Primary Examiner* — Kamran Afshar
*Assistant Examiner* — Ying Yu Chen
(74) *Attorney, Agent, or Firm* — Nolan M. Lawrence

(57) ABSTRACT

Solved diagnosis case data is stored by utilizing a redundant discrimination net as a dynamic memory. The stored diagnosis case data is incorporated to form scientific descriptions within a medical knowledge base and heuristics within an empirical knowledge base. Diagnosis hypotheses are generated using an initial symptom description, the dynamic memory, and the medical knowledge base. The initial symptom description is received from an end user. A subset of the diagnosis hypotheses is created to form one or more solution cases. The one or more solution cases are presented to a subject matter expert. A diagnosis success or a diagnosis failure identifying, based on a response received from the subject matter expert, to form an assessed solution case. An assessed solution case is converted into experiences. The experiences are inputted into the dynamic memory. Data containing the assessed solution case is transmitted to a medical artificial intelligence analytics application.

20 Claims, 12 Drawing Sheets

(51) Int. Cl.
*G16H 70/60* (2018.01)
*G16H 50/70* (2018.01)
*G06N 5/02* (2006.01)

(56) References Cited

U.S. PATENT DOCUMENTS

| | | | |
|---|---|---|---|
| 6,527,713 | B2 | 3/2003 | Iliff |
| 6,571,251 | B1 | 5/2003 | Koski et al. |
| 7,899,764 | B2 | 3/2011 | Martin et al. |
| 8,296,247 | B2 | 10/2012 | Zhang et al. |
| 8,337,409 | B2 | 12/2012 | Iliff |
| 8,548,828 | B1 | 10/2013 | Longmire |
| 8,805,756 | B2 * | 8/2014 | Boss ............ G06Q 50/00 706/12 |
| 9,153,142 | B2 | 10/2015 | Bagchi et al. |
| 9,265,416 | B2 | 2/2016 | Klin et al. |
| 9,594,878 | B2 | 3/2017 | Silva et al. |
| 10,223,640 | B2 | 3/2019 | Magro et al. |
| 2014/0279746 | A1 | 9/2014 | De Bruin et al. |
| 2015/0066378 | A1 | 3/2015 | Robison et al. |
| 2015/0310177 | A1 * | 10/2015 | Csurka ............ G06N 5/04 706/50 |
| 2016/0259893 | A1 | 9/2016 | Bessette |
| 2019/0043610 | A1 | 2/2019 | Vaughan |
| 2019/0104982 | A1 | 4/2019 | Dunn et al. |

OTHER PUBLICATIONS

Travis Goodwin and Sanda M. Harabagiu, "Automatic Generation of a Qualified Medical Knowledge Graph and its Usage for Retrieving Patient Cohorts from Electronic Medical Records", 2013, 2013 IEEE Seventh International Conference on Semantic Computing, pp. 363-370. (Year: 2013).*

Trang Pham, Truyen Tran, Dinh Phung and Svetha Venkatesh, "DeepCare: A Deep Dynamic Memory Model for Predictive Medicine", arXiv, Apr. 10, 2017, pp. 1-27. (Year: 2017).*

Hossein Mohammadhassanzadeh, William Van Woensel, Samina Raza Abidi, and Syed Sibte Raza Abidi, "Semantics-based plausible reasoning to extend the knowledge coverage of medical knowledge bases for improved clinical decision support", Feb. 10, 2017, BioData Mining (2017) 10:7; pp. 1-31. (Year: 2017).*

Beatriz López, Cartes Pous, Pablo Gay, Albert Pla, Judith Sanz, and Joan Brunet, "eXiT*CBR: A framework for case-based medical diagnosis development and experimentation", Oct. 25, 2010, Artificial Intelligence in Medicine 51 (2011), pp. 81-91. (Year: 2010).*

Maximilian Nickel, Kevin Murphy, Volker Tresp, and Evgeniy Gabrilovich, "A Review of Relational Machine Learning for Knowledge Graphs", Jan. 2016, vol. 104, No. 1 | Proceedings of the IEEE, pp. 11-33. (Year: 2016).*

Alkim et al., "A Fast and Adaptive Automated Disease Diagnosis Method with an Innovative Neural Network Model," Neural Networks, vol. 33, Sep. 2012, pp. 88-96, http://www.sciencedirect.com/science/article/pii/S0893608012001268, © 2012 Elsevier Ltd.

Amato et al., "Artificial Neural Networks in Medical Diagnosis," Journal of Applied Biomedicine, vol. 11, Issue 2, 2013, pp. 47-58, http://www.sciencedirect.com/science/article/pii/S1214021X14600570.

Firger, J., "12 million Americans misdiagnosed each year," CBS News, http://www.cbsnews.com/news/12-million-americans-misdiagnosed-each-year-study-says/, 4 pgs., Apr. 17, 2014, 5:00 AM, printed Feb. 23, 2017.

Kolodner, J., "An Introduction to Case-Based Reasoning," Artificial Intelligence Review 6, 3-34, 1992, 32 pgs., http://alumni.media.mit.edu/~jorkin/generalsipapers/Kolodner_case_based_reasoning.pdf.

Mell et al., "The NIST Definition of Cloud Computing," Recommendations of the National Institute of Standards and Technology, U.S. Department of Commerce, Special Publication 800-145, Sep. 2011, 7 pgs.

Patra et al., "An Expert System for Diagnosis of Human Diseases," International Journal of Computer Applications (0975-8887), vol. 1, No. 13, pp. 71-73, © 2010.

Accelerated Examination Support Document, U.S. Appl. No. 15/893,130, signed Feb. 1, 2018, 24 pgs.

List of IBM Patents or Patent Applications Treated as Related, Feb. 6, 2018, 2 pgs.

* cited by examiner

UTILIZING ARTIFICIAL INTELLIGENCE FOR DATA EXTRACTION

BACKGROUND

The present invention relates generally to the field of data processing, and more particularly to artificial intelligence.

Artificial intelligence is an area of computing dedicated to enabling computers to exhibit intelligence. A computing device may utilize artificial intelligence to mimic cognitive functions, such as machine learning and natural language processing. Automated reasoning is a subset of artificial intelligence that may utilize artificial intelligence techniques effectively to more efficiently carry out tasks performed by a computing device.

SUMMARY

Embodiments of the present invention disclose a method, computer program product, and system for generating ailment, disorder, and disease diagnostic data for consumption by a medical artificial intelligence analytics application. Solved diagnosis case data is stored by utilizing a redundant discrimination net as a dynamic memory. The stored diagnosis case data is incorporated to form scientific descriptions within a medical knowledge base and heuristics within an empirical knowledge base. Diagnosis hypotheses are generated using an initial symptom description, the dynamic memory, and the medical knowledge base. The initial symptom description is received from an end user. A subset of the diagnosis hypotheses is created to form one or more solution cases. The one or more solution cases are presented to a subject matter expert. A diagnosis success or a diagnosis failure identifying, based on a response received from the subject matter expert, to form an assessed solution case. An assessed solution case is converted into experiences. The experiences are inputted into the dynamic memory. Data containing the assessed solution case is transmitted to a medical artificial intelligence analytics application.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
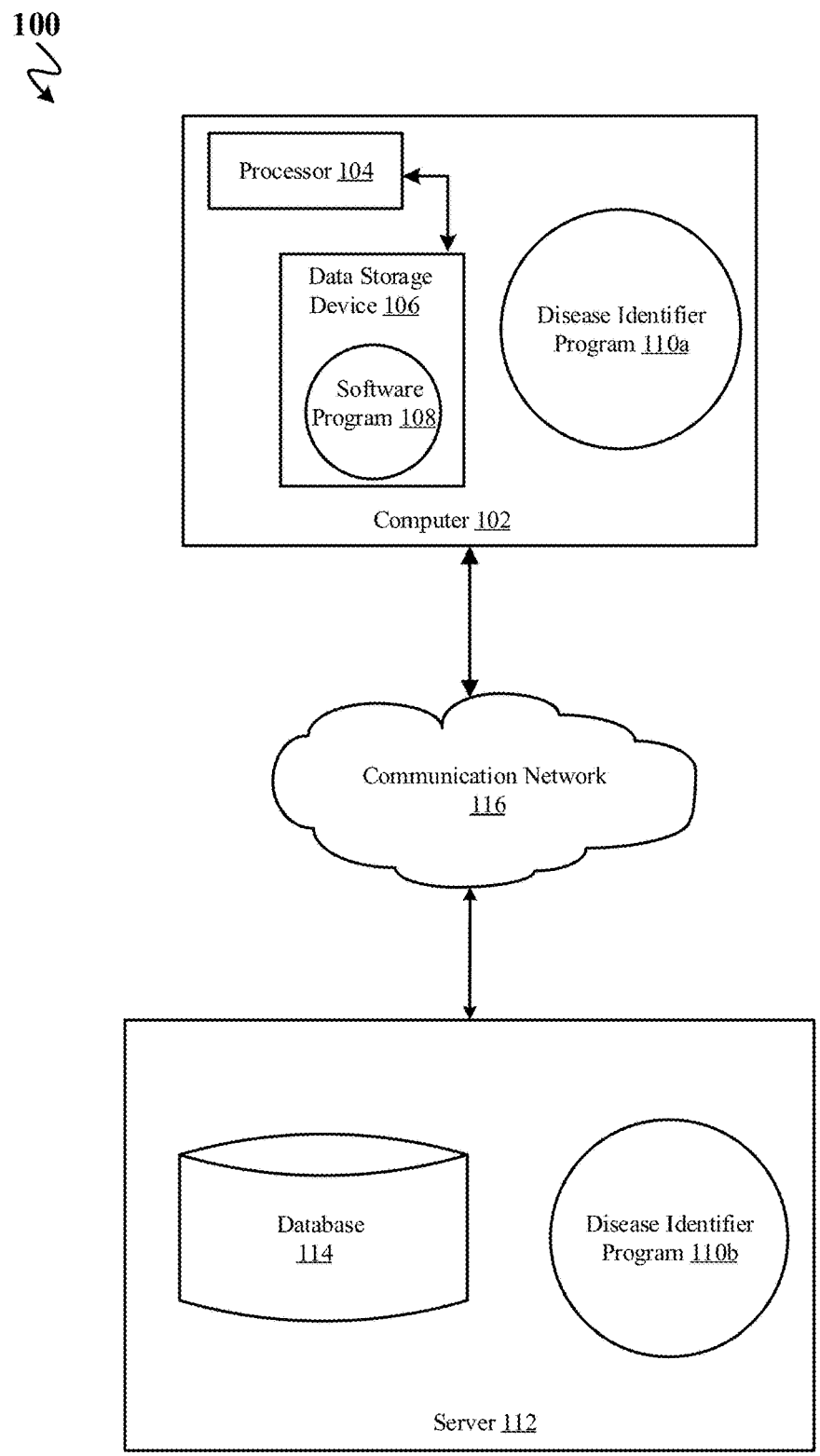
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Web search tools are becoming more efficient every day. People are constantly looking for information on the Internet about different topics. When people get sick, it is common that before visiting a doctor they perform Internet searches about the symptoms they have, in order to understand what is going on with them, and then formulate a self-diagnosis. A thoughtful self-diagnosis may require large amounts of information to be analyzed and interpreted properly. This task, however, is not an easy undertaking for a patient with minimal to no medical background, and even at some basic level of knowledge, performing self-diagnosis may be a poor idea.

As a patient studies more about their condition from disparate sources, they may be stressed by concluding they have diseases that they actually do not have. This situation can affect their ability to explain what they feel to a professional, thereby providing the doctor with misinformation, and the doctor may arrive at an inaccurate diagnosis. In the patient's distress, he may create vague and imprecise symptomatic descriptions, concentrating more on the obvious, observable symptoms, but overlooking other developing and critical symptoms that may require immediate attention. Moreover, in moments of fear, patients may also need to communicate their condition and receive responses in terms that they can readily understand. The current lack of mechanisms able to handle both formal medical knowledge (e.g., knowledge derived from scientific research) and empirical medical knowledge (e.g., knowledge derived more from experience-heuristics than from formal scientific rigor) to help patients in these types of situations, may lead to an incorrect diagnosis.

On the other hand, it is probable that doctors may initially diagnose based on the misinformation provided by a patient already influenced by the incorrect diagnosis created in their mind. Doctors therefore may need the assistance of some mechanism that can help them quickly diagnose, validate, or confirm a certain patient condition. One obvious way to achieving a diagnosis with some degree of certainty may be for doctors to request all possible studies currently available to gather more information about the patient's condition. However, this is costly for healthcare plans. Therefore, before prescribing the appropriate tests, an artificial intelligence system can come to the rescue.

Although peer doctors, medical publication, and other medical sources contribute to a diagnosis, an interactive tool that could quickly serve as guide in moments of uncertainty would be of great benefit for both doctor and patient. An additional benefit from this interactive tool is that it could also capture all the information involved in the diagnosing process, leaving no information forgotten to memory. Organized correctly as a live, up to date, learning knowledge base, the information in this interactive tool can be used to solve subsequent similar cases, adapt it to discover new situations, and be used for research and data analysis purposes.

Further, providing disease diagnosis data to analytics tools may come at a great expense. For one, such data may not be quite as available. Additionally, transforming and cleaning the data may require a considerable amount of knowledge, time, and effort. The need for automated mechanisms able to capture expert medical knowledge and use it in ways that produce timely, detailed, and concise data is becoming increasingly important for cost-effective research. Expert knowledge in the domain of disease diagnosis needs to be organized in ways that it can be used by an artificial intelligence system to interactively guide both patients and doctors to effectively identify diseases, disorders, and medical conditions based on possibly incomplete and vague user-provided symptomatic descriptions.

In some embodiments, the results of disease identifications may be validated by subject matter experts and then be incorporated to the knowledge base as new learning data for the disclosed artificial intelligence system. This may not only improve the artificial intelligence system's performance on a continuous basis, but can also be shared with external analytics tools. More specifically, aspects of the present disclosure may compare the inputted symptoms to cases stored in case memory, transform content of the received symptoms into data structures, determine that the inputted symptoms satisfy a diagnosis threshold, then provide the user with a diagnosis description. Moreover, aspects of the present disclosure may receive subject matter expert verification of any generated diagnosis descriptions. Additionally, aspects of the present disclosure may export cases stored in case memory to analytics system administrators.

Automated reasoning is a discipline of artificial intelligence that has been used to solve problems in the classification of domains. In general, such systems are composed of three knowledge bases: a formal knowledge base, an empirical knowledge base, and a case memory. A formal knowledge base may be scientific information about a particular knowledge area (e.g., diseases, infections, etc.), and provided by a subject matter expert (e.g., a medical expert). In the classification domain, this information is best organized as a tree data structure, whose levels represent categories or types. General concepts are then located as nodes at the top levels of the tree data structure, while specific concepts are nodes placed in lower levels. This knowledge base should not be empty. An empirical knowledge base includes heuristic information related to the knowledge area at hand, and provided by the subject matter expert (e.g., the medical expert). This knowledge base may be empty upon system initialization. Case memory includes dynamic, self-organizing, redundant net data structures containing information of previously solved problems related to the knowledge area at hand. The case memory is composed of norms (nodes that represent generalizations of some concepts), cases (previously solved problems), and indices (pointers to norms and cases). The terms dynamic and self-organizing refer to the case memory's capability to accept experiences (i.e., new solution cases that result from adaptations of previously stored cases with new information) and incorporate them as new learning elements. This knowledge base may be empty upon system initialization.

Automated reasoning systems may utilize a learning process that includes ingesting, analyzing, evaluating, and determining. Machine learning performed by an artificial intelligence system may become more precise and efficient at solving problems, and therefore, establish patterns and may make determinations that are more accurate. Aspects of the present disclosure utilize automated reasoning as an inference and learning approach to propose a system, called the disease identifier (DI), that implements an automated reasoning approach to solving diagnosis cases of ailments, disorders, and diseases. In some embodiments, the DI further utilizes a redundant discrimination net as dynamic memory for storing solved diagnosis cases. Additionally, the DI may incorporate diagnostic-supporting data, known as a medical knowledge base, in the form of scientific descriptions (e.g., formal knowledge base) and heuristics (e.g. empirical knowledge base) of ailments, disorders, and diseases.

Moreover, the DI may interact with a user (e.g., a patient), among others, who describes symptoms and, using both the dynamic memory and the medical knowledge base, may generate diagnosis hypotheses. The DI may then create a subset of the diagnostic hypotheses as solution cases, and then present the solution cases to the user and/or others. The DI may then present the solution cases to the subject matter expert (e.g., a doctor or medical expert), who may determine their diagnosis success or failure. The DI may then convert the assessed solution cases to experiences that are fed into the dynamic memory, which in turn, runs a self-organizing process to incorporate the new knowledge and improve performance in future diagnostic case sessions. The DI may then propose corrections and enhancements to the medical knowledge base by analyzing the incorporated new knowledge against existing descriptions and heuristics. Additionally, the DI may compress, convert, and then export data containing updated and validated solution case data, in formats such that can be easily consumed by medical artificial intelligence analytics applications.

A new set of methods may produce valid disease databases that may be consumed by an artificial intelligence system. Aspects of the present disclosure may reduce the data curation stage on the medical artificial intelligence analytics application side. Furthermore, by repeated usage, increases in the knowledge base may be accomplished automatically using machine learning, and improve diagnosis performance. Aspects of the present disclosure may also have the ability to export first-hand, up to date, and concise diagnosis data retrieved from the system, and further produce cost-effective, reliable medical data from direct sources: users and experts. Feeding a medical artificial intelligence analytics application with this data can increase its effectiveness (e.g., the speed and accuracy of the artificial intelligence analytics application), and therefore offer accurate disease decisions and treatment alternatives.

The following described exemplary embodiments provide a system, method, and program product for utilizing an automated reasoning approach for diagnosing a disease. As such, embodiments of the present disclosure may improve the technical field of automated health informatics and diagnosis by determining a disease, given a patient's inputted-symptoms, and then comparing the symptoms to symptoms stored in a database. More specifically, embodiments may automatically ingest, utilizing, e.g., a natural language processor, a patient's symptoms, then create a tree graph of the symptoms, determine the patient's disease within a confidence interval checked by a medical professional, then store the determined disease within a database for future use. Additionally, the artificial intelligence system may compress, convert, and then export the ingested and analyzed data to an artificial intelligence system. By compressing, converting, and exporting the data to the artificial intelligence systems, embodiments of the present disclosure may also improve the speed, accuracy, and effectiveness of the artificial intelligence systems.

It is to be understood that the aforementioned advantages are example advantages and should not be construed as limiting. Embodiments of the present disclosure can contain all, some, or none of the aforementioned advantages while remaining within the spirit and scope of the present disclosure.

Referring to FIG. 1, an exemplary networked computer environment 100 in accordance with at least one embodiment is depicted. The networked computer environment 100 may include a computer 102 with a processor 104 and a data storage device 106. Computer 102 is enabled to run a software program 108 and a disease identifier program 110a. The networked computer environment 100 may also include a server 112 that is enabled to run a disease identifier program 110b that may interact with a database 114 and a communication network 116. The networked computer environment 100 may include one or more computers 102 and one or more servers 112, only one of each of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 9, server 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database. According to various implementations of the present embodiment, the disease identifier program 110a, 110b may interact with a database 114 that may be embedded in various storage devices, such as, but not limited to a computer/mobile device 102, a networked server 112, or a cloud storage service. The database 114 can include a repository of any transactions associated or initiated with the disease identifier program 110a and 110b. The disease identifier program 110a and 110b may be updated in any system associated with the disease identifier program 110a and 110b (e.g., database 114).

According to the present embodiment, a user using a client computer 102 or a server computer 112 may use the disease identifier program 110a, 110b (respectively) to receive an initial symptom description inputted by a user, transform the initial symptom description into data structures, compare the transformed data structures to cases comprising data structures stored in case memory, then determine a disease based on the data structures satisfying a threshold.

Figure 2:
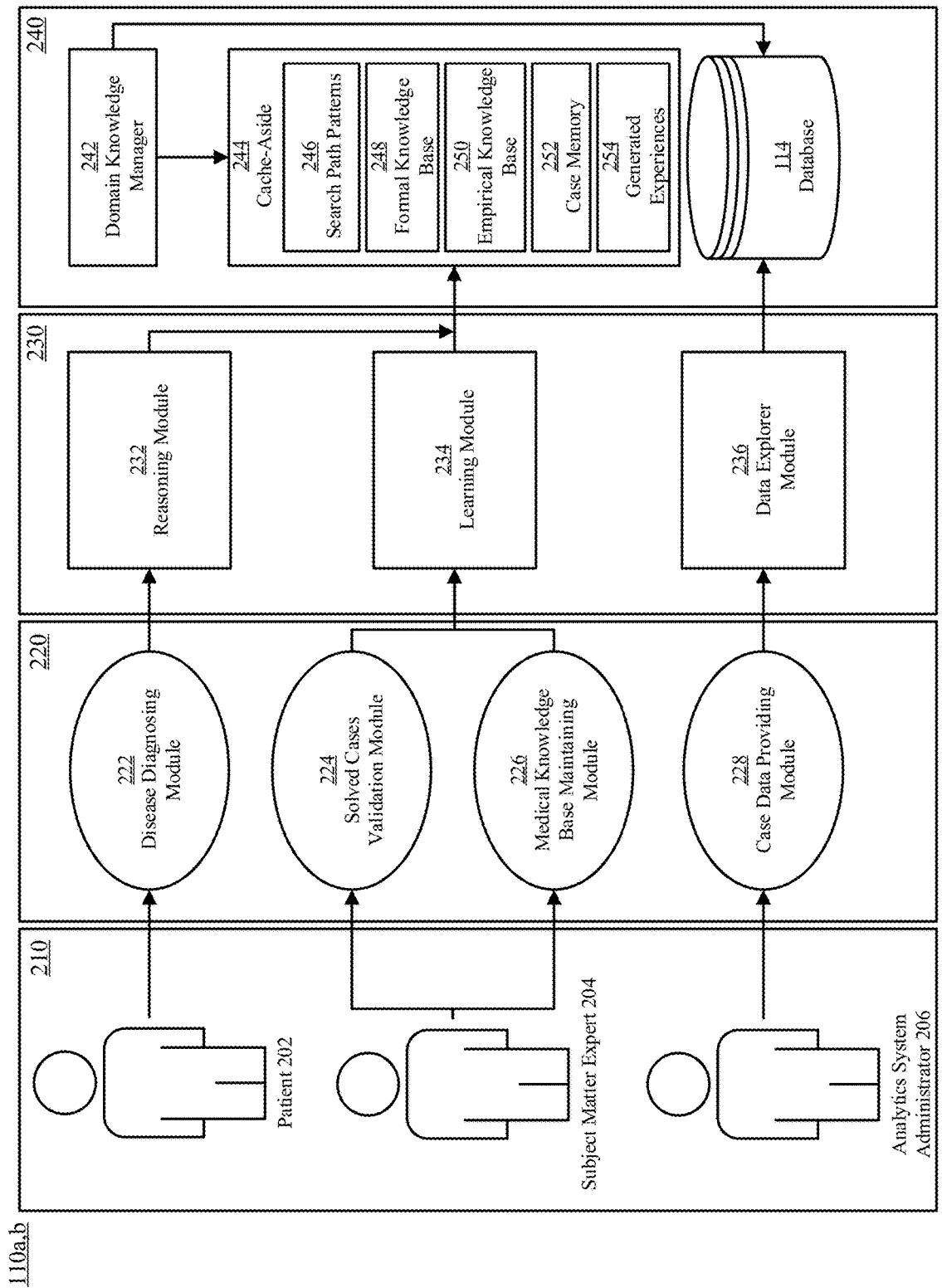
FIG. 2 illustrates an exemplary architecture overview of a disease identifier program according to at least one embodiment.

FIG. 2 is a block diagram of an architecture overview of the disease identifier program 110a, b, according to embodiments of the present disclosure. The disease identifier program 110a, b may include a consumer tier 210, a services tier 220, a service component tier 230, and an operational systems tier 240. The consumer tier 210 may include a patient 202 (e.g., a user), a subject matter expert 204 (e.g., a medical expert or a doctor), and an analytics systems administrator 206 (e.g., a technician, an artificial intelligence analytics application, etc.). The services tier 220 may include a disease diagnosing module 222, solved cases validation module 224, medical knowledge base maintaining module 226, and case data providing module 228. The service components tier may include a reasoning module 232, a learning module 234, and a data explorer module 236. The operational systems tier 240 may include a domain knowledge manager 242, a cache-aside 244 that includes: search path patterns 246, formal knowledge base 248, empirical knowledge base 250, case memory 252, and generated experiences 254; and, the database 114. Following is an explanation of various embodiments of the disease identifier program 110 a, b.

The patient 202 may be a person experiencing symptoms or someone acting on their behalf (e.g., a doctor). The patient 202 may provide the disease diagnosing module 222 with an initial symptom description. The inputted initial description may be in the form of text, audio, and/or video. The initial symptom description may include elements that have no particular ordering, and which can range from long and detailed to short and fuzzy. The problem description may include "free-form" descriptive elements (i.e., elements that are not necessarily part of the formal knowledge base 248). The disease identifier program 110a and 110b analyzes the initial symptom description and, using previously recorded, weighted, and successful search patterns from past solution cases, decides on one or more search paths stored in search path patterns 246. These search paths may include traversing any combination of the case memory 252 (priority may be given to this base when available), the formal knowledge base 248 (priority may be given to this base when the case memory 252 is empty), or the empirical knowledge base 250.

Additionally, the disease diagnosing module 222 may organize and normalize the inputted symptoms into different categories, and then utilize natural language processing to transform the organized symptoms in the form of text, audio, or video into structured data. In some cases, the disease diagnosing module 222 may be or include a natural language processor. The disease diagnosing module 222 may be a computer module that performs lexical analysis, and may convert a sequence of characters into a sequence of tokens. A token may be a string of characters included in written passage and categorized as a meaningful symbol. Further, disease diagnosing module 222 may identify word boundaries in content and break any text passages within the content into their component text elements, such as words, multiword tokens, numbers, and punctuation marks. In some embodiments, the disease diagnosing module 222 may receive a string of characters, identify the lexemes in the string, and categorize them into tokens.

Consistent with various embodiments, the disease diagnosing module 222 may include a computer module that marks up a word in passages submitted by the patient 202 to correspond to a particular part of speech. The disease diagnosing module 222 may read a passage or other text in natural language and assign a part of speech to each word or other token. The disease diagnosing module 222 may determine the part of speech to which a word (or other text element) corresponds based on the definition of the word and the context of the word. The context of a word may be based on its relationship with adjacent and related words in a phrase, sentence, or paragraph. In some embodiments, the context of a word may be dependent on one or more previously analyzed content (e.g., the content of one disease or symptom may shed light on the meaning of text elements in related diseases or symptoms). Examples of parts of speech that may be assigned to words include, but are not limited to, nouns, verbs, adjectives, adverbs, and the like. Examples of other part of speech categories that disease diagnosing module 222 may assign include, but are not limited to, comparative or superlative adverbs, wh-adverbs, conjunctions, determiners, negative particles, possessive markers, prepositions, wh-pronouns, and the like. In some embodiments, the disease diagnosing module 222 may tag or otherwise annotate tokens of a passage with part of speech categories.

In some embodiments, the disease diagnosing module 222 may include a computer module that may be configured to identify semantic relationships of recognized text elements (e.g., words, phrases) in received content. In some embodiments, the disease diagnosing module 222 may determine functional dependencies between entities and other semantic relationships. Consistent with various embodiments, the disease diagnosing module 222 may be configured to identify syntactic relationships in a passage composed of tokens. The disease diagnosing module 222 may determine the grammatical structure of sentences such as, for example, which groups of words are associated as phrases and which word is the subject or object of a verb. The disease diagnosing module 222 may conform to formal grammar. The disease diagnosing module 222 may then transmit the structured data to the reasoning module 232 to be formatted in such a way that the structured data may be compared to stored previously solved cases, or cases stored in memory (e.g., case memory 252). The reasoning module 232 may traverse search paths in search path patterns 246 to go through case memory 252 based on the initial symptom description.

According to an embodiment, when the initial problem description may be insufficient, or does not satisfy a threshold, (e.g., there were not enough descriptive elements to retrieve solved cases), the search process may halt at an intermediate point within the corresponding data structures (e.g., case memory 252). In this case, the system may analyze and retrieve relevant successor nodes and use this information to guide the patient 202 by providing questions aimed at observing and providing information that is more descriptive. For example, the disease diagnosing module 222 may display a questionnaire with any incomplete questions, requesting the patient 202 to fill out the questionnaire. The disease diagnosing module 222 may then provide the questionnaire to the reasoning module 232 to use the completed questionnaire to continue advancing the search for relevant cases. If the patient 202 cannot provide further information, the reasoning module 232 may choose to back track to a previous node and choose a different search path.

According to some embodiments, if the initial problem description yielded some cases, but some descriptive elements were left out, the disease diagnosing module 222 may use the surplus descriptive elements to search the formal knowledge base 248 in an effort to discover cases never processed before. The disease diagnosing module 222 may guide the patient 202 with questions aimed at observing and providing more descriptive information. In an event that advancing through the case memory 252 comes to a halt, the disease diagnosing module 222 may choose to back track to a previous node and choose a different search path. If all surplus descriptive elements were considered, but there are still some of them that were not processed because they are new, and thus unknown, to the disease diagnosing module 222, the disease diagnosing module 222 may attempt to match them against the empirical knowledge base 250 in order to further continue the search and guidance process.

All retrieved cases from the case memory 252, the formal knowledge base 248, and the empirical knowledge base 250 may constitute solution hypotheses. All hypotheses may be analyzed and weighted, and redundancies may be removed. The resulting hypotheses with the highest weights may be the most likely viable solutions. A solution may be positive, that is, a case that has the probability of being successful, or it may be negative, meaning that the system could not find potentially successful solutions, but offers cases that the disease diagnosing module 222 determines may not be successful alternatives and thus not worth pursuing further. The disease diagnosing module 222 may propose the selected solution hypotheses to the patient 202. The disease diagnosing module 222 may create new cases that may utilized when creating a new diagnosis description (to be discussed with reference to FIG. 8), which may be adaptations of the old, retrieved cases with the entire "solution path," that are search paths ending in a particular solution, produced by the initial problem description plus all the process steps. In some embodiments, only experiences that strictly have new information to the case memory 252 are considered.

These generated experiences may be stored in generated experiences 254, along with the solution path, and may be verified by the subject matter expert 204 or retrieved by the analytics system administrator 206 (e.g., an artificial intelligence analytics application). These experiences are ready for expert validation (e.g., the subject matter expert 204) before being incorporated by the learning module 234 to the case memory 252 as new solution cases. A case may be considered solved when the disease diagnosing module 222 provides the patient 202 with a disease based on the initial symptom description. The learning module 234 may create experiences, adapt information from past cases to new experiences, and store experiences in the database 114, formal knowledge base 248, or empirical knowledge base 250, for the subject matter expert 204 to determine whether the created experience is valid.

The subject matter expert 204 (e.g., a medical scientist, doctor, or artificial intelligence application) may validate all solved diagnosis cases utilizing the solved case validation module 224 and the medical knowledge base maintaining module 226. The subject matter expert 204 may manage the formal knowledge base 248 to check that stored information is accurate. The subject matter expert 204 may manually mark the solved cases as positive or negative after inspection, or the solved cases validation module 224 may automatically mark the solved cases based on historical records of the subject matter expert's 204 past marks. The solved cases validation module 224 may mark cases solved by the disease identifier program 110 a, b (e.g., experiences) as positive or negative, and discard redundancies (experiences that already exist in case memory 252). The system may present the subject matter expert 204 with solved cases that have not yet been evaluated.

For one or more experiences, the subject matter expert 204 may analyze and evaluate the initial symptom description, the solution description, and the set of outcomes presented to the patient 202. The subject matter expert 204 may then determine whether the experience was a success or failure. In the event that there are new descriptive elements, the subject matter expert 204 may proceed to update the corresponding elements in the case memory 252 with this new information. In the event that new descriptive elements can be expressed in terms of heuristics, the subject matter expert 204 may proceed to update the empirical knowledge base 250 with this new information. The subject matter expert 204 may then signal the solved cases validation module 224 or the medical knowledge maintaining module 226 to save all updated data. The system may then save the data to the database 114 or to case memory 252 and then proceed to reorganize the case memory 252 and update indices as necessary.

The medical knowledge base maintaining module 226 may keep the empirical knowledge base 250 up to date with the latest scientific and empirical data inputted by the subject matter expert 204, or ingested automatically by the medical knowledge base maintaining module 226 (e.g., from medical websites, scientific papers, published studies, etc.). The subject matter expert 204 may select either the empirical knowledge base 250 or the formal knowledge base 248 to analyze. The medical knowledge maintaining module 226 may then present the subject matter expert 204 with the selected knowledge base (i.e., the empirical knowledge base 250 or the formal knowledge base 248). The subject matter expert 204 (or the medical knowledge base maintaining module 226 itself) may then update diseases, symptoms, symptom synonyms, and heuristics within the empirical knowledge base 250 or the formal knowledge base 248, as appropriate, by adding new data, or modifying and deleting existing data. The subject matter expert 204 may signal the system to save all updated data. The medical knowledge maintaining module 226 may then save the data to the database 114, the empirical knowledge base 250, or the formal knowledge base 248, and then proceed to update indices located within case memory 252 as necessary.

The analytics system administrator 206 may be an automated user (e.g., a medical artificial intelligence analytics application) that may request solved case data stored in memory (e.g., database 114) for analysis and research. Case data providing module 228 may provide solved case data as requested by an analytics system administrator 206, or a medical artificial intelligence analytics application. The data explorer module 236 may follow the search paths in an effort to retrieve a set of relevant cases from the database 114 or case memory 252 using the initial symptom description as a search basis. The analytics system administrator 206 may request a data subset from the case data providing module 228 that has cases that satisfy a given set of parameters. For example, the cases may include cancer patients aged 24-50 years old or patients with diabetes living within a particular city. The analytics system administrator 206 may also request the data subset be in a particular type of file (e.g., .pdf, .doc, .exe, etc.), the data to be compressed, the data to be written in a certain programming language (e.g., C+, Java, etc.), the data being presented with a particular schema, or the data to be translated to a different format (e.g., audio, text, or video). The case data providing module 228 may transmit the requested data subset to the data explorer module 236. The data explorer module 236 may search for and then retrieve case data from the database 114. The retrieved data is provided in the format requested by the analytics system administrator 206. The case data providing module 228 may send the requested data to the analytics system administrator 206 in the certain type of file as requested by the analytics system administrator 206.

A cache-aside 244 may be an architectural pattern for cloud, composed by the domain knowledge manager 242, and the data structures needed for the inference and learning processes may keep properly updated instances of those data structures to help improve performance. The cache-aside 244 may also ensure that consistency is maintained between the cache and the data in the underlying database 114, and the multi-tenancy and elastic scaling properties of cloud can be incorporated in a system design.

Figure 3A:
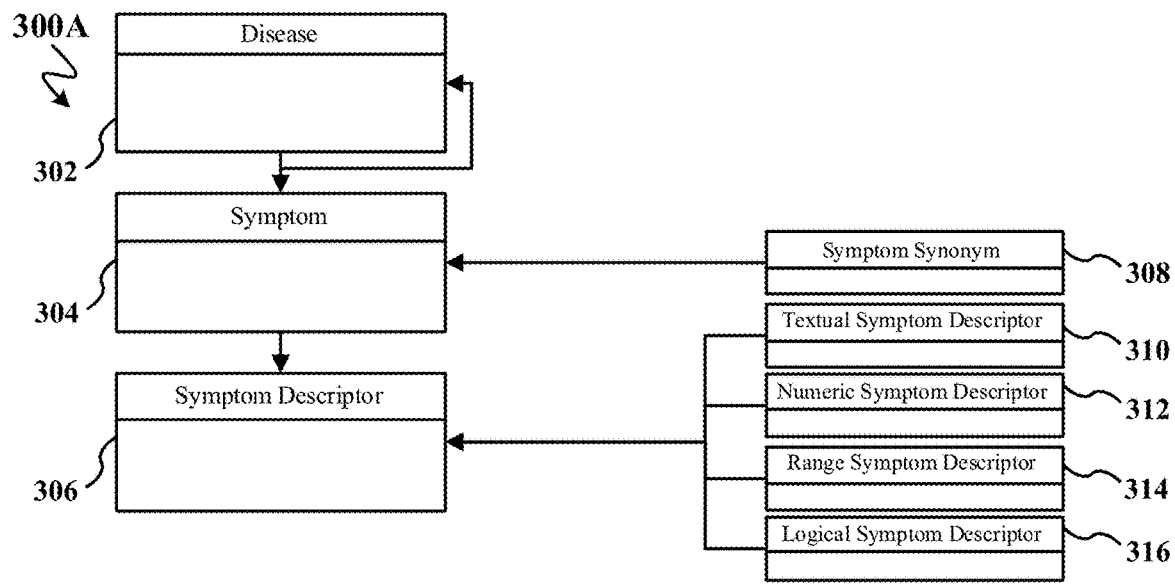
FIG. 3A illustrates an exemplary domain model of a formal knowledge base according to at least one embodiment.

Referring now to FIG. 3A, shown is an exemplary domain model 300A of the formal knowledge base 248. The exemplary domain model 300A depicts an exemplary disease hierarchy composed of one or more indices: disease 302, symptom 304, symptom descriptor 306, symptom descriptor 308, textual symptom descriptor 310, numeric symptom descriptor 312, range symptom descriptor 314, and logical symptom descriptor 316. The disease hierarchy may be tree data structures whose nodes are instances of a disease class. A purpose for using these data structures may be to organize diseases into categories, also known as disease subtypes, ranging from the most general disease definitions at upper levels to the most concrete disease definitions at lower levels. The tree can be composed of an arbitrary number of levels, and each node may have an arbitrary number of successors (zero or more disease sub types). A disease node with no predecessor is the root of the tree (e.g., disease 302).

A disease instance (e.g., disease 302) may include a name, a description, and a non-empty set of symptoms. A symptom instance (e.g., symptom 304) may include a name, a description, a weight, a non-empty set of instances of symptom descriptors (e.g., symptom descriptor 306), and a possibly empty set of instances of symptom synonyms (e.g., symptom synonyms 308). The symptom descriptor 306 provides a value that a symptom may have with respect to a particular disease. These values may be textual (e.g., textual symptom descriptor 310), numeric (e.g., numeric symptom descriptor 312), a numeric range (e.g., range symptom descriptor 314), and/or logical (e.g., Boolean) (e.g., logical symptom descriptor 316). Moreover, symptom descriptor 306 may also be described by a weight that indicates how important a symptom is with respect to a disease, and how important symptom descriptor 306 is with respect to the symptom 304. These values may be used during the search and inference processes to determine precedence among solution hypothesis candidates. The symptom synonym 308 is an alternate name for a symptom, usually a commonly used, non-scientific name (e.g., skin cancer as an alternate for melanoma).

Figure 3B:
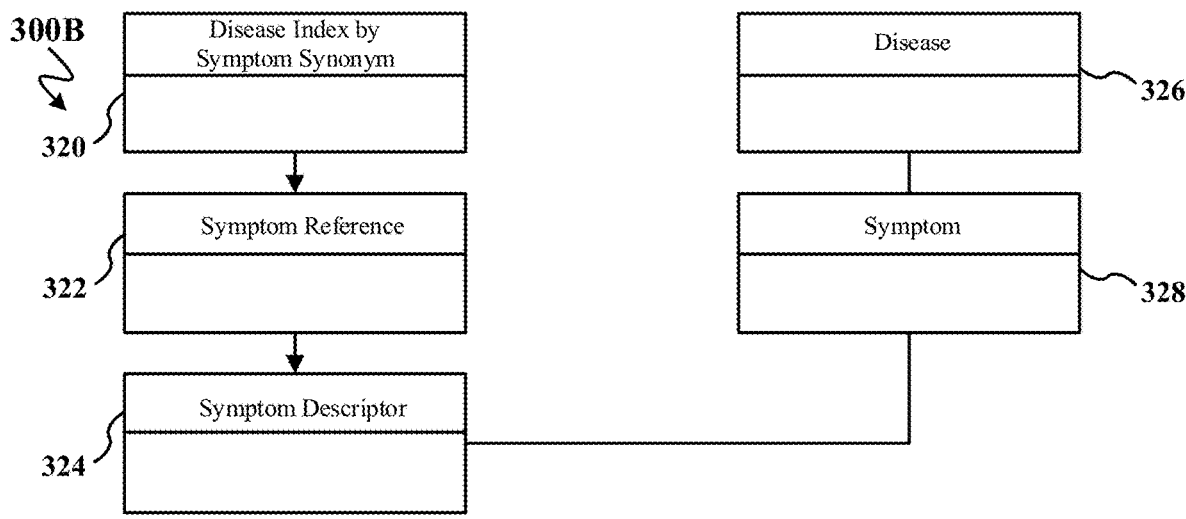
FIG. 3B illustrates another exemplary domain model of the formal knowledge base according to at least one embodiment.

Traversing a data tree is a costly operation. Therefore, indices may be used to ensure acceptable disease-search response times from the system. Referring now to FIG. 3B, shown is an exemplary domain model 300B of the formal knowledge base 248. The exemplary domain model 300B depicts an exemplary disease index by symptom descriptor 320. The disease index by symptom descriptor 320 is data structures that hold an ordered set of instances of symptom references (e.g., symptom reference 322). Every instance of a symptom reference 322 may hold a unique symptom name and an ordered set of all possible references to the symptom descriptor 324 contained in symptoms with the same name. The symptom descriptor 324 may include a link to associated symptoms 328, and the associated symptoms 328 may include a link to associated diseases 326.

Figure 3C:
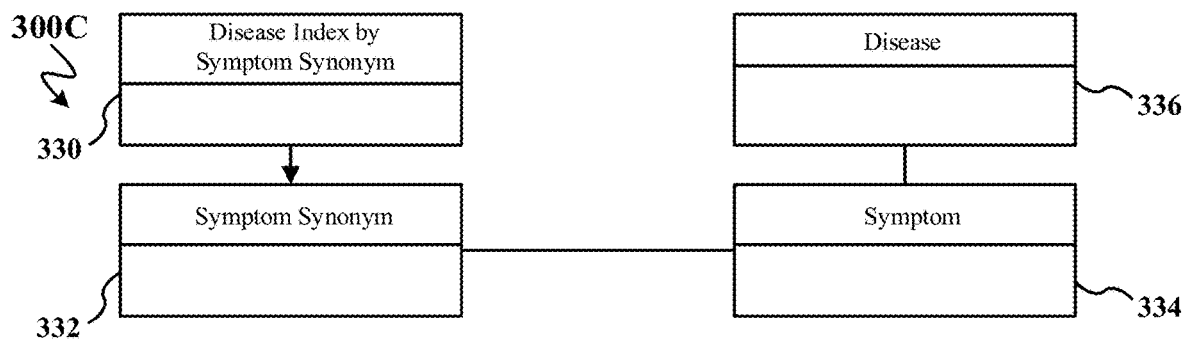
FIG. 3C illustrates yet another exemplary domain model of the formal knowledge base according to at least one embodiment.

Referring now to FIG. 3C, shown is an exemplary domain model 300C of the formal knowledge base 248. The exemplary domain model 300C depicts an exemplary disease index by symptom synonym 330. The disease index by symptom synonym 330 is data structures that hold an ordered set of all possible references to symptom synonym 332 within the disease hierarchy. The symptom synonym 332 may include a link to associated symptoms 334, and the associated symptom 334 may include a link to associated disease 336.

Figure 4A:
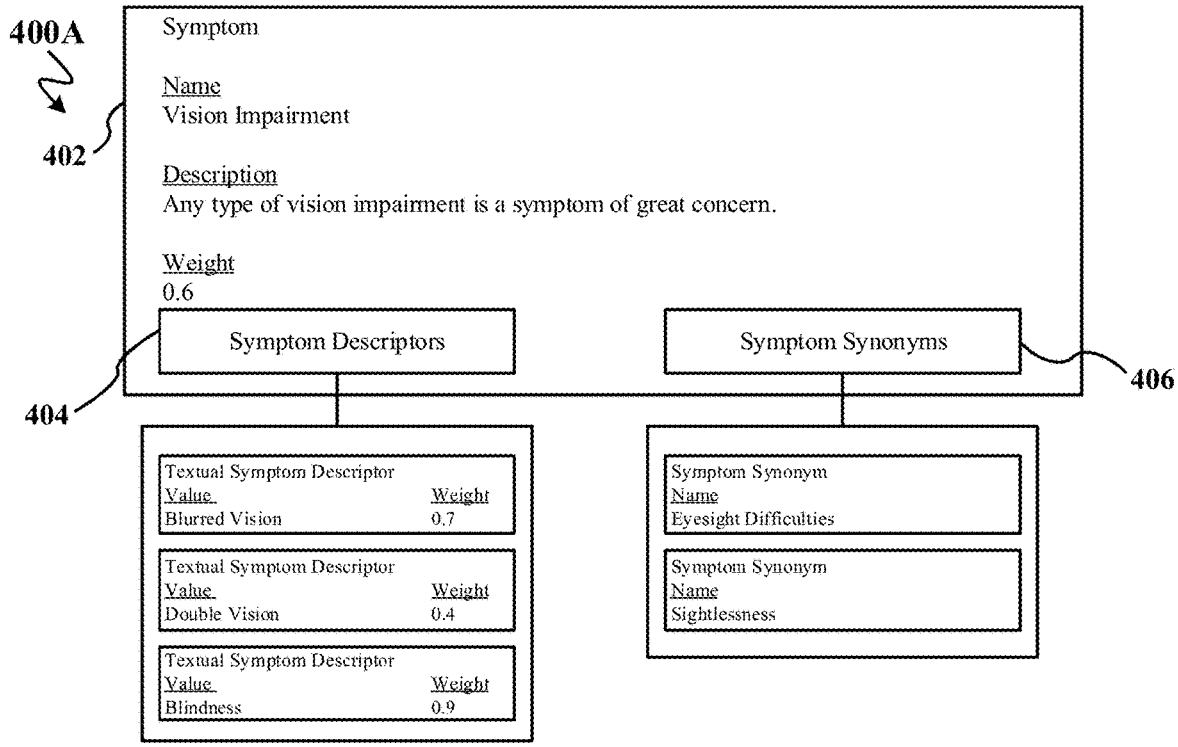
FIG. 4A illustrates an exemplary implementation model of a formal knowledge base according to at least one embodiment.

Referring now to FIG. 4A, an exemplary implementation model 400A of the formal knowledge base 248 is depicted as a visual representation of a symptom 402, and associated symptom descriptors 404 and symptom synonyms 406. A description of the symptom 402 may include a name, a description of the symptom, and a weight that indicates the importance of a particular symptom. The visual representation may also include symptom descriptors 404 that include a value (e.g., blurred vision, double vision, and blindness) and a weight of each corresponding value. The visual representation may also include symptom synonyms 406 that include commonly used names of the symptom name, vision impairment (e.g., eyesight difficulties, sightlessness).

Figure 4B:
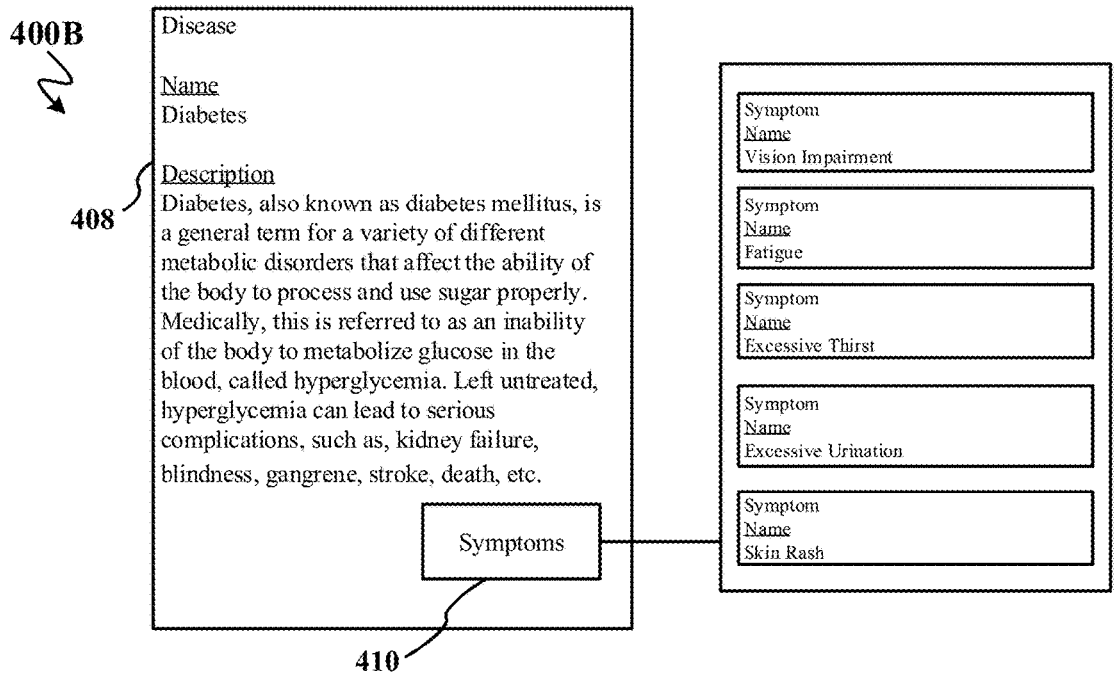
FIG. 4B illustrates another exemplary implementation model of the formal knowledge base according to at least one embodiment.

Referring now to FIG. 4B, an exemplary implementation model 400B of the formal knowledge base 248 is depicted as a visual representation of a disease 408 and associated symptoms 410. The visual representation of the disease 408 may include a name and a description of the disease that gives a brief background of the disease. The disease symptoms 410 may include any number of symptoms associated with the disease.

Figure 5:
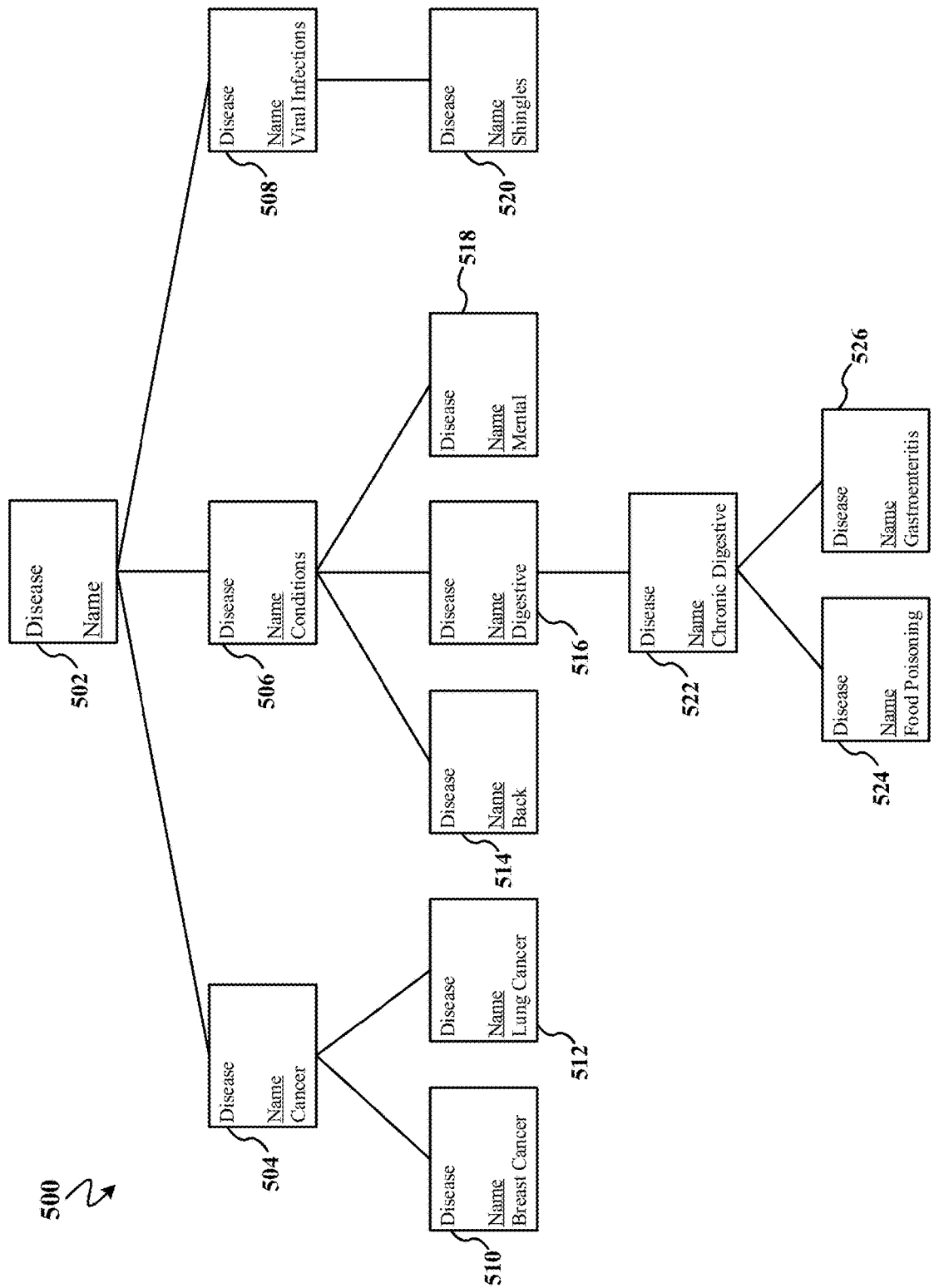
FIG. 5 illustrates a disease hierarchy in the form of a disease data tree according to at least one embodiment.

Referring now to FIG. 5, an exemplary disease hierarchy in the form of a disease data tree 500 is depicted, according to various embodiments. The disease data tree 500 may be stored in the cache-aside 242, particularly the formal knowledge base 248 or the empirical knowledge base 250, or the database 114. The root node 502 is depicted as a disease. The root node 502 may have one or more child nodes: cancer node 504, conditions node 506, and viral infections node 508. The child nodes 504, 506, and 508 may organize the root node 502 (e.g., parent node) according to types. The disease 502 may include any number of child nodes. The number of disease child nodes may depend of an availability of relevant disease information located in the cache-aside 244 or the database 114. Each disease type may include one or more child nodes. For example, the cancer node 504 may include two child nodes: a breast cancer node 510 and a lung cancer node 512. The conditions node may include three child nodes: a back node 514, a digestive node 516, and a mental node 518. The viral infections node may include a child node: a shingles node 520. The digestive node may include a child chronic-digestive node 522 that includes two child nodes: a food poisoning node 524 and a gastroenteritis node 526.

Figure 6A:
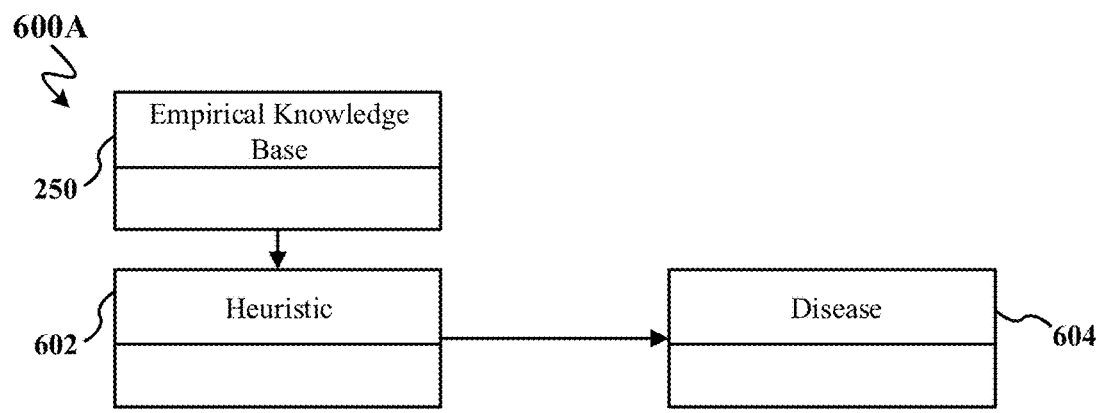
FIG. 6A illustrates an exemplary empirical knowledge base in the form of an implementation model according to at least one embodiment.

Referring now to FIG. 6A, an exemplary empirical knowledge base 250 in the form of an implementation model 600A is depicted, according to various embodiments. The empirical knowledge base 250 may be data structures that hold a set of heuristic instances 602. A heuristic instance 602 may be a generalized conclusion about a disease, which may be represented as disease index 604, which may be the result of non-scientific observation and experimentation. A heuristic instance 602 may also be the result of "popular knowledge" about a particular disease.

Figure 6B:
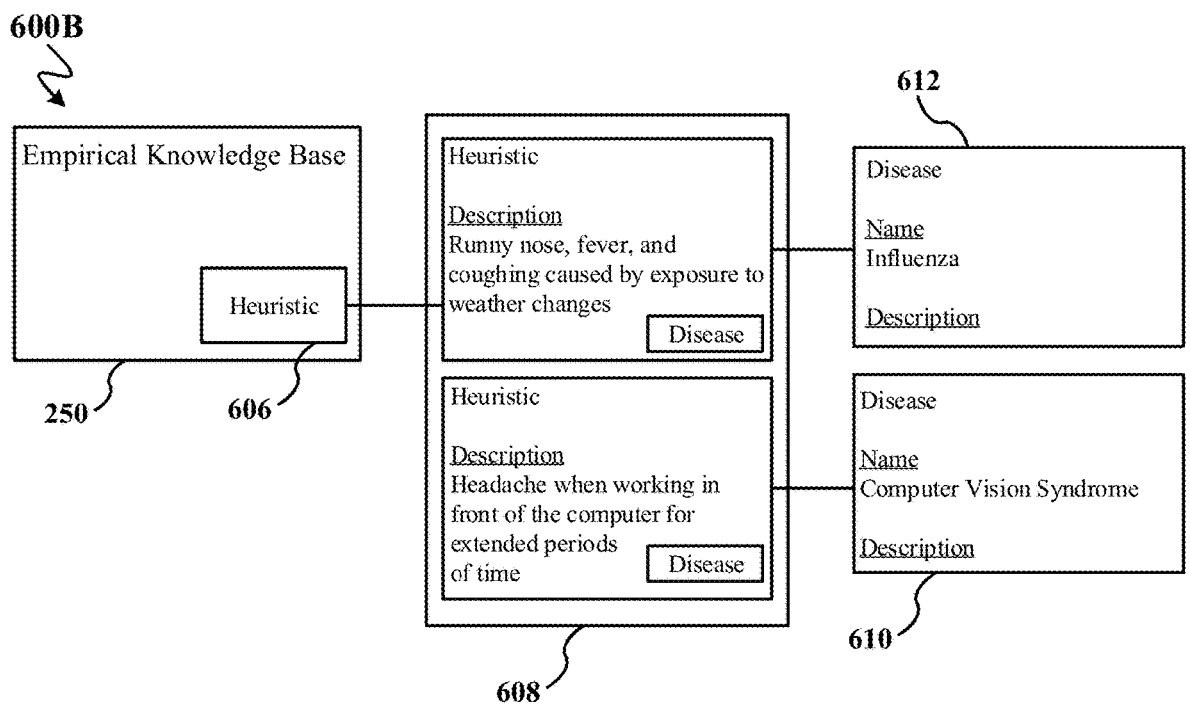
FIG. 6B illustrates another exemplary empirical knowledge base in the form of an implementation model according to at least one embodiment.

Referring now to FIG. 6B, an exemplary empirical knowledge base 250 in the form of an implementation example 600B is depicted, according to various embodiments. The exemplary empirical knowledge base 250 may include a heuristic instance 606 that is linked to popular beliefs about a particular disease 608. The two linked popular beliefs 608 may each include a description, and their associated diseases 610, 612. The associated diseases 610, 612 may be linked to each heuristic popular belief 608: influenza 612 and computer vision syndrome 610, each heuristic popular belief 608 may also include a name and description.

Figure 7A:
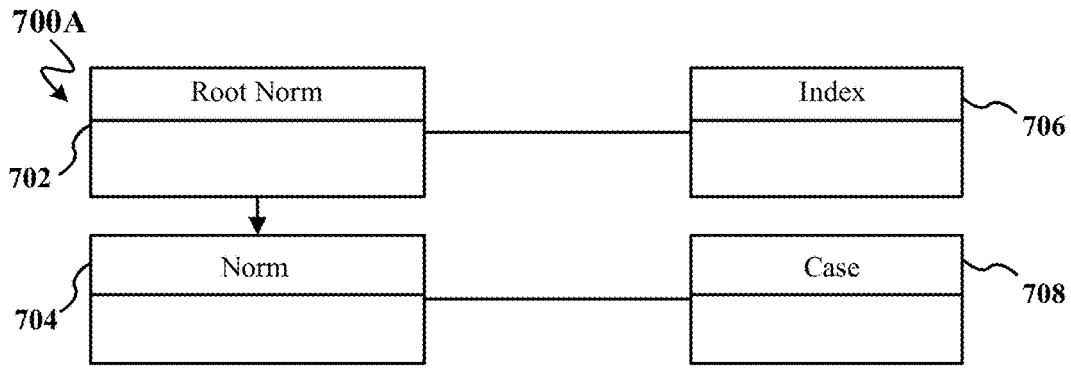
FIG. 7A illustrates an exemplary indices graph of case memory according to at least one embodiment.

Referring now to FIG. 7A, an exemplary indices graph 700A of case memory 252 is depicted, according to various embodiments. A root norm 702 may be an entry point to the case memory 252. The root norm 702 may include a set of index instances 706. A norm 704 that may be connected to the root norm 702 may be an intermediate, or internal, node that serves as an abstraction element (e.g., generalization and grouping of cases containing the same symptom references, discussed with reference to FIG. 3A). A norm 704 may also contain a set of index instances 706, and cases 708 (e.g., previously solved cases and cases inputted by a subject matter expert 204).

Figure 7B:
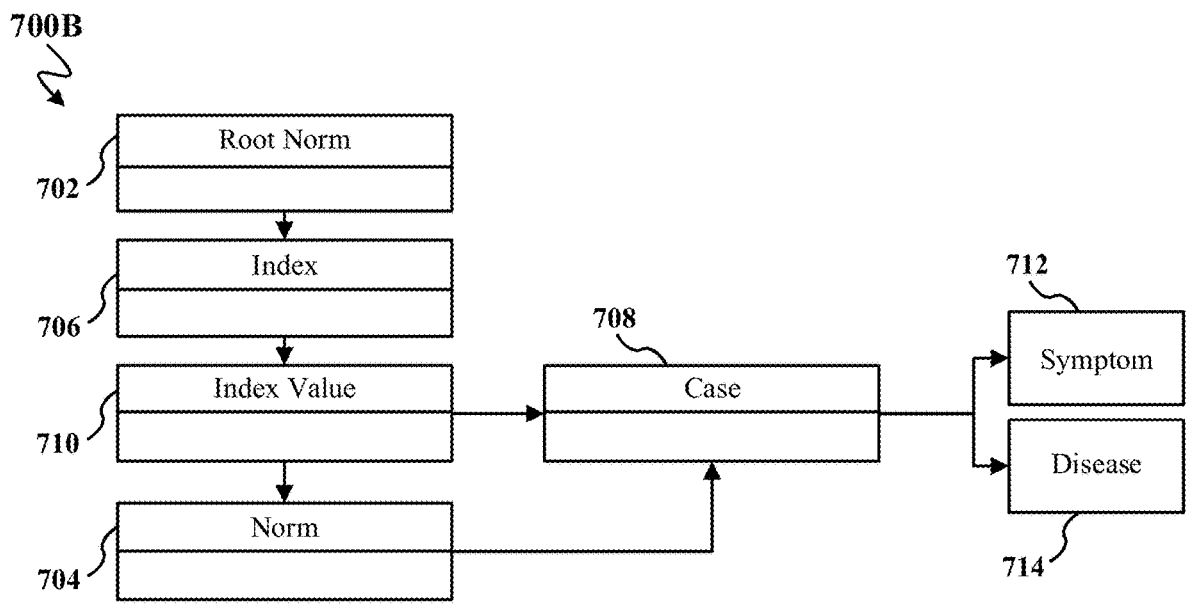
FIG. 7B illustrates an exemplary diagram of case memory according to at least one embodiment.

Referring now to FIG. 7B, an exemplary diagram 700B of case memory 252 is depicted, according to various embodiments. The first level node of the case memory 252 may be the root norm 702 (i.e., the source of the graph). An index 706 may be a referencing structure composed of a symptom name, which is part of a solution path of one or more cases (e.g., case 708), such as a symptom 712 or a disease 714, and a non-empty set of index value instances. An index value may hold one value for the referenced symptom, and this value may be either textual, numeric, a number range, or logical. With this value, the index value points either to a non-empty set of cases (e.g., 708), or to a lower-level norm 704 instance.

A norm 704 is an internal node of the graph. A case 708 is a piece of information that represents an experience. This experience may teach the disease identifier program 110 a,

*b* a fundamental identification lesson in disease diagnosis. In other words, a case 708 holds information of how a disease identification problem was solved by way of its solution path (e.g., the solution description that may be symptom attributes collected by case memory 252 traversal from the root norm 702 to the case 708). As such, a case 708 may then be a terminal node (e.g., a sink of the graph). The resulting graph may be, in consequence, a redundant discrimination net composed of sub nets organized by internal and terminal nodes according to the values of multiple indices. The term redundant deals with the fact that, as a result of the graph's structural organization, terminal nodes (e.g., cases 708) may be accessed through diverse paths.

Figure 7C:
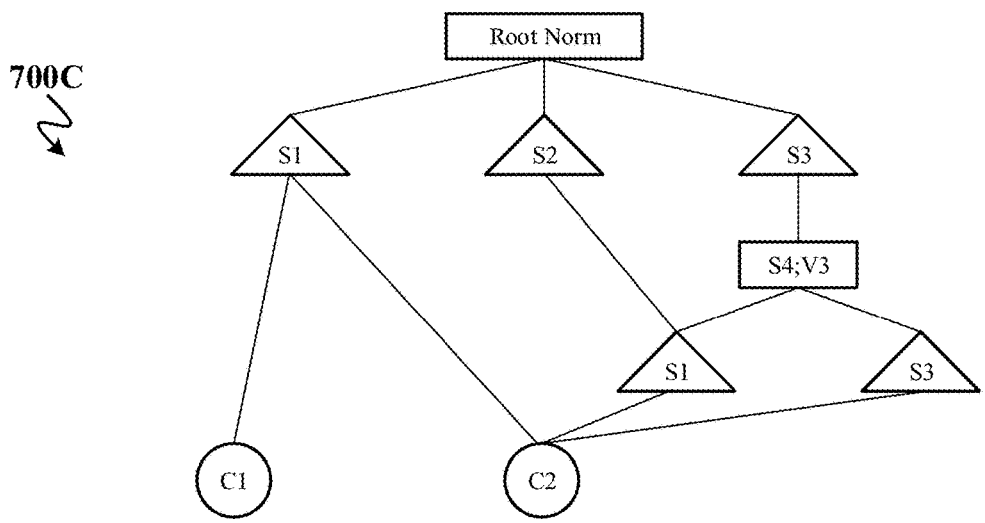
FIG. 7C illustrates an exemplary diagram of a case memory graph according to at least one embodiment.

Referring now to FIG. 7C, an exemplary diagram 700C of a case memory graph implementation is depicted, according to various embodiments. The rectangle labeled root norm may be an entry point, or source, to the case memory graph 252. The lines may represent an index value containing the value for the symptom referenced by the containing index. The triangles may represent an index holding a symptom name. The case memory graph includes three different symptoms: S1, S2, and S3; and, values represented as the lines. A rectangle that includes S4;V3 may represent a norm including a generalization of a <symptom, value> pair found in two or more case solution descriptions. A solved case, and sink of the case memory graph may be represented as C1 and C2. A solution for C1 may be <S1,V1>, and a solution for C2 may be <S1,V2>, <S1,V1>, and <S3,V4>.

Figure 8:
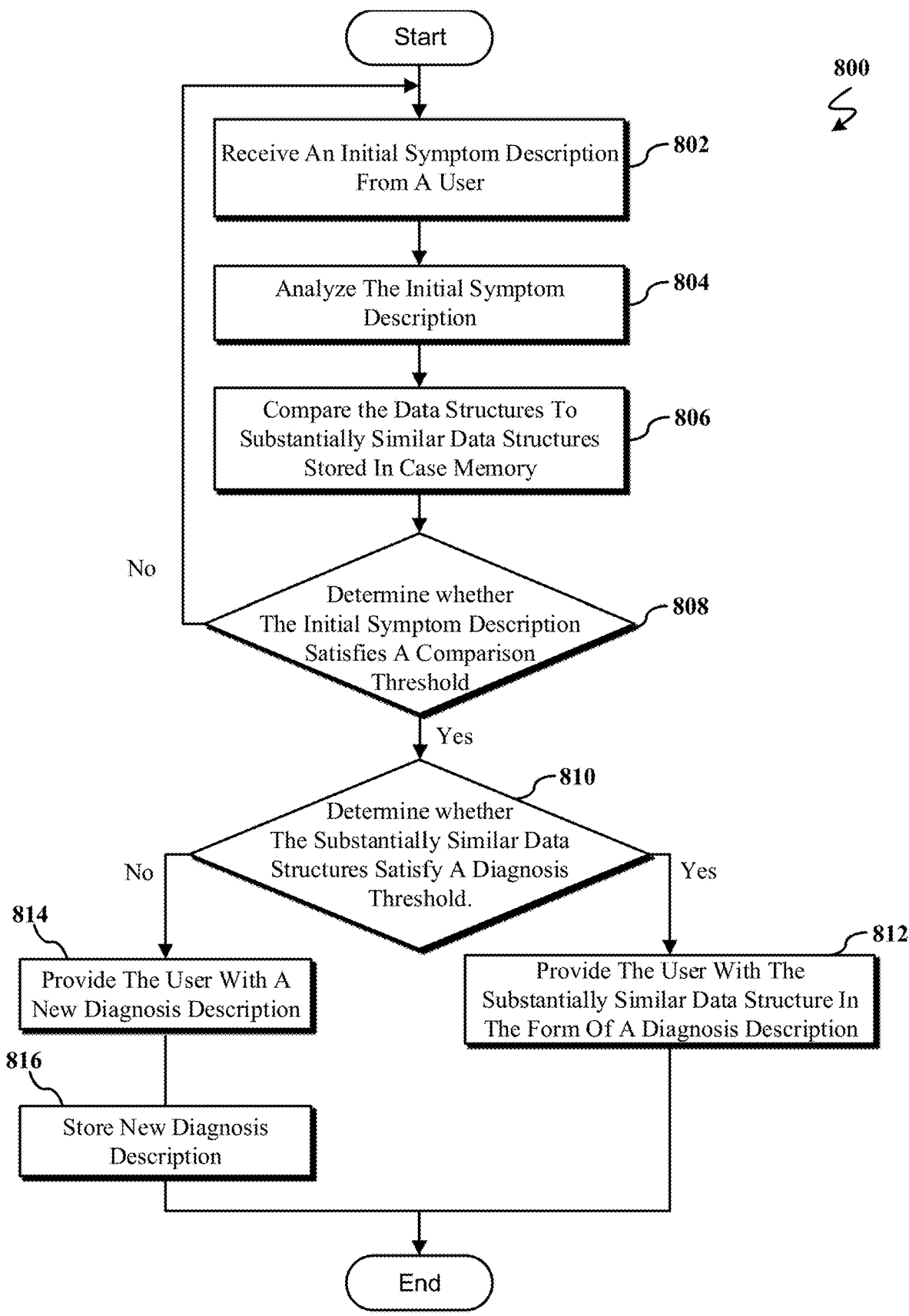
FIG. 8 illustrates an operational flowchart illustrating an example disease diagnosis process by a disease identifier program according to at least one embodiment.

Referring now to FIG. 8, an operational flowchart illustrating an exemplary disease diagnosis process 800, according to at least one embodiment, is depicted. The process 800 may be executed by a processor (e.g., the disease identifier program 110a and 110b shown in FIG. 1). At 802, the disease identifier program 110a and 110b receives an initial symptom description from a user. The user may be a patient (e.g., patient 202). The initial symptom description may be a problem description, whose descriptive elements have no particular ordering, and which can range from long and detailed to short and fuzzy. The problem description may include "free-form" descriptive elements. The inputted initial description may be in the form of text, audio, and/or video, and in any language (e.g., French or Russian). For example, the user may load the disease identifier program 110a and 110b, and describe the symptoms he is having into a microphone, or into a web camera, or point the webcam to display a rash or infected area of himself.

At 804, the disease identifier program 110a and 110b analyzes the initial symptom description. The disease identifier program 110a and 110b may analyze the initial symptom description and, using previously recorded, weighted, and successful search patterns from past solution cases, decide on one or more search paths. These search paths may include traversing any combination of the case memory 252 (priority may be given to this base when available), the formal knowledge base 248 (priority may be given to this base when the case memory is empty), or the empirical knowledge base 250. In some cases, the disease identifier program 110a and 110b may include a natural language processor, may perform lexical analysis, and may convert a sequence of characters into a sequence of tokens. The disease identifier program 110a and 110b may organize and normalize the inputted symptoms into different categories, and then utilize natural language processing to transform the organized symptoms in the form of text, audio, or video into structured data.

According to at least one embodiment, the disease identifier program 110a and 110b may be or include a natural language processing system capable of executing entity resolution techniques that may be helpful in identifying important entities within the initial symptom description. Entity resolution techniques may identify concepts and keywords within an initial symptom description. Once entities have been identified, correlations and linguistic links between entities may be detected and used to establish relevance of the entities and, ultimately, the context of the initial symptom description. An example technique that may be useful in determining the relative importance of a given entity to the context of the passage is inverse document frequency, which utilizes the relative commonality of the entity as an indicator of its importance to evaluating context. Many other techniques may also be used. These same techniques may be useful for determining the symptoms or critical words of the initial symptom description and then identifying synonyms or antonyms.

The text elements may be any words in the form of text that appears more than once or have a relative importance to the initial symptom description. The text elements may have also been transformed into text from an audio or video format by utilizing speech to text or video/image analysis to generate the corresponding text, which can then be parsed. The text elements may be a concept within the text of the initial symptom description or within an audio and video recording within the initial symptom description. The parsed text elements or keywords of the initial symptom description may be included more than once and may be a different font (e.g., larger than other words within the user selected messages) or presented in a different manner than other words within the initial symptom description (e.g., bolded or in italics). Additionally, the text element and/or keywords may be listed in a table for visual view to the user. The table may be ordered based on user pre-configuration (e.g., most important to least important).

At 806, the disease identifier program 110a and 110b compares the data structures form the initial symptom description to data structures stored in case memory 252, the formal knowledge base 248, and the empirical knowledge base 250 to identify data structures that are substantially similar. One or more cases within the case memory 252, the formal knowledge base 248, and the empirical knowledge base 250 may constitute one or more solution hypotheses that include the substantially similar data structures. The one or more solution hypotheses may be analyzed, weighted, and have redundancies removed. The resulting hypotheses with the highest weights may be the most likely viable solutions. A solution may be positive, that is, a case that has a high probability of being successful (e.g., greater than a threshold), or it may be negative, meaning that the disease diagnosing module 222 determines it may not be successful and thus not worth pursuing further (e.g., does not satisfy the threshold).

At 808, the disease identifier program 110a and 110b determines whether the initial symptom description satisfies a comparison threshold. The comparison threshold is a numerical representation of the similarity between the data structures form the initial symptom description to data structures stored in case memory 252, the formal knowledge base 248, and the empirical knowledge base 250. The numerical representation may be any positive number and may signal that the initial symptom description includes enough detail so that the disease identifier program 110 *a, b* may generate a diagnosis description. The comparison threshold may be satisfied if the comparison threshold exceeds a predetermined numerical value that may be any positive number. If the disease identifier program 110a and 110b determines the substantially similar data structures satisfy the comparison threshold (808, "YES" branch), the disease diagnosis process 800 may determine whether the substantially similar data structures satisfy a diagnosis threshold at 810. The diagnosis threshold is a numerical representation of the similarity between the data structures form the initial symptom description and data structures of a previous diagnosis. The numerical representation may be any positive number. The diagnosis threshold being satisfied may signal that the initial symptom description matches a previous initial symptom description, or data structures included in a previous diagnosis, so that a new diagnosis description need not be generated. The diagnosis threshold may be satisfied if the diagnosis threshold exceeds a predetermined numerical value that may be any positive number. If the disease identifier program 110a and 110b determines the substantially similar data structures do not satisfy a threshold (808, "NO" branch), the disease diagnosis process 800 may continue to receive additional input from the user to add to the initial symptom description.

If the disease identifier program 110a and 110b determines the initial symptom description does not satisfy the threshold, then, at 802, the disease identifier program 110a and 110b receives additional input from the user to add to the initial symptom description. When the initial symptom description may be insufficient (e.g., there were not enough descriptive elements to retrieve solved cases within case memory 252), the disease diagnosis 800 process may halt at an intermediate point within the corresponding data structures (e.g., case memory 252 or disease hierarchy). In this case, the disease identifier program 110a and 110b may then analyze and then retrieve relevant successor nodes and use this information to guide the patient 202 by providing questions aimed at observing and providing information that is more descriptive. For example, the disease diagnosing module 222 may display a questionnaire with any incomplete questions, requesting the patient 202 to fill out the questionnaire. The disease diagnosing module 222 may then provide the questionnaire to the reasoning module 232 to use the complete questionnaire to continue advancing the search for relevant cases. If advancing through the corresponding data structures comes to a halt because the patient 202 cannot provide further information, the reasoning module 232 may choose to back track to a previous node and choose a different search path.

However, if the disease identifier program 110a and 110b determines the initial symptom description does satisfy the comparison threshold, then, at 810, the disease identifier program 110a and 110b determines whether the substantially similar data structures satisfy a diagnosis threshold. If the disease identifier program 110a and 110b determines the substantially similar data structures satisfy the diagnosis threshold (810, "YES" branch), the disease diagnosis process 800 may provide the user the substantially similar data structures in the form of a diagnosis at 812. If the disease identifier program 110a and 110b determines the substantially similar data structures do not satisfy the diagnosis threshold (810, "NO" branch), the disease diagnosis process 800 may continue to provide the user a new diagnosis at operation 814.

If the disease identifier program 110a, b determines the substantially similar data structures satisfy the diagnosis threshold, then, at 812, the disease identifier program 110a, b provides the user with the substantially similar data structures in the form of a diagnosis description at operation 812. The diagnosis description may be in the form of the exemplary implementation model 400A. The diagnosis description may include a name of a disease that has substantially similar symptoms as the initial symptom description, and may include related symptoms. The diagnosis description may also include a case, and a digital representation (e.g., a graph tree of the case) of the case may be provided. Additionally, the diagnosis description may include more than one disease. The more than one diseases may be diseases that had substantially similar cases, but were weighted less than the highest weighted disease, or disease that were included in case memory that did not satisfy the diagnosis threshold. The diagnosis description may be displayed within a client device (e.g., computer 102). A link to a medical journal or dictionary where the source information for the case was extracted from may be provided with the diagnosis description. Once the disease identifier program 110a, b provides the user with the substantially similar data structures in the form of a diagnosis description, the disease diagnosis process 800 may terminate.

However, if the disease identifier program 110a, b determines the substantially similar data structures do not satisfy the diagnosis threshold, then, at 814, the disease identifier program 110a, b provides the user with a new diagnosis description. The new diagnosis description may be adaptations of the old, retrieved cases with the entire "solution path," which are search paths ending in a particular solution, produced by the initial symptom description. The new diagnosis description may also include a case, and a digital representation (e.g., a graph tree of the case) of the case may be provided. Additionally, the new diagnosis description may include more than one disease. The more than one diseases may be diseases that had substantially similar cases, but were weighted less than the highest weighted disease, or disease that were included in case memory that did not satisfy the diagnosis threshold. The diagnosis description may be displayed within a client device (e.g., computer 102). A link to a medical journal or dictionary where the source information for the case was extracted from may be provided with the new diagnosis description. The new diagnosis description may be provided with a confidence interval indicating a degree of confidence that the new diagnosis description is a correct diagnosis, given the initial symptom description compared to the cases stored in case memory. The confidence interval may be determined utilizing known statistical techniques, commonly known in the art.

At 816, the disease identifier program 110a, b stores the new diagnosis description. The new diagnosis description may be stored in the cache-aside 244, more particularly generated experiences 254, or in the database 114. The confidence interval may be stored with the new diagnosis description, and then validated by the subject matter expert 204. Experiences that strictly have new information to the case memory 252 may be considered. These experiences may be ready for expert validation before being incorporated by the learning module 234 to the case memory 252 as new solution cases. A case may be considered solved when the disease diagnosing module 222 provides the patient 202 with a disease based on the initial inputted symptom description. The learning module 234 may create experiences, adapt information from past cases to new experiences, and then store experiences in the database 114, formal knowledge base 248, or empirical knowledge base 250, for the subject matter expert 206 to determine whether the created experience is valid. Once approved by the subject matter expert 204, the new diagnosis description may be used as a case for future use. The analytics system administrator 206 may retrieve the new diagnosis description from the database 114. After disease identifier program 110a, b stores the new diagnosis description at 816, the disease diagnosis process 800 may terminate.

In some embodiments, if the initial problem description yields some cases, but some descriptive elements were left out from the initial symptom description, the disease diagnosing module 222 may use the surplus descriptive elements to search the formal knowledge base 248 in an effort to discover cases never processed before. The disease diagnosing module 222 may guide the patient 202 with questions aimed at observing and providing more descriptive information. If advancing through the disease hierarchy comes to a halt, the disease diagnosing module 222 may choose to back track to a previous node and choose a different search path.

In some embodiments, if surplus descriptive elements were considered, but there are still some of them that were not processed because they are new to the disease diagnosing module 222, the disease diagnosing module 222 will attempt to match them against the empirical knowledge base 250 in order to further continue the search and guidance process.

Figure 9:
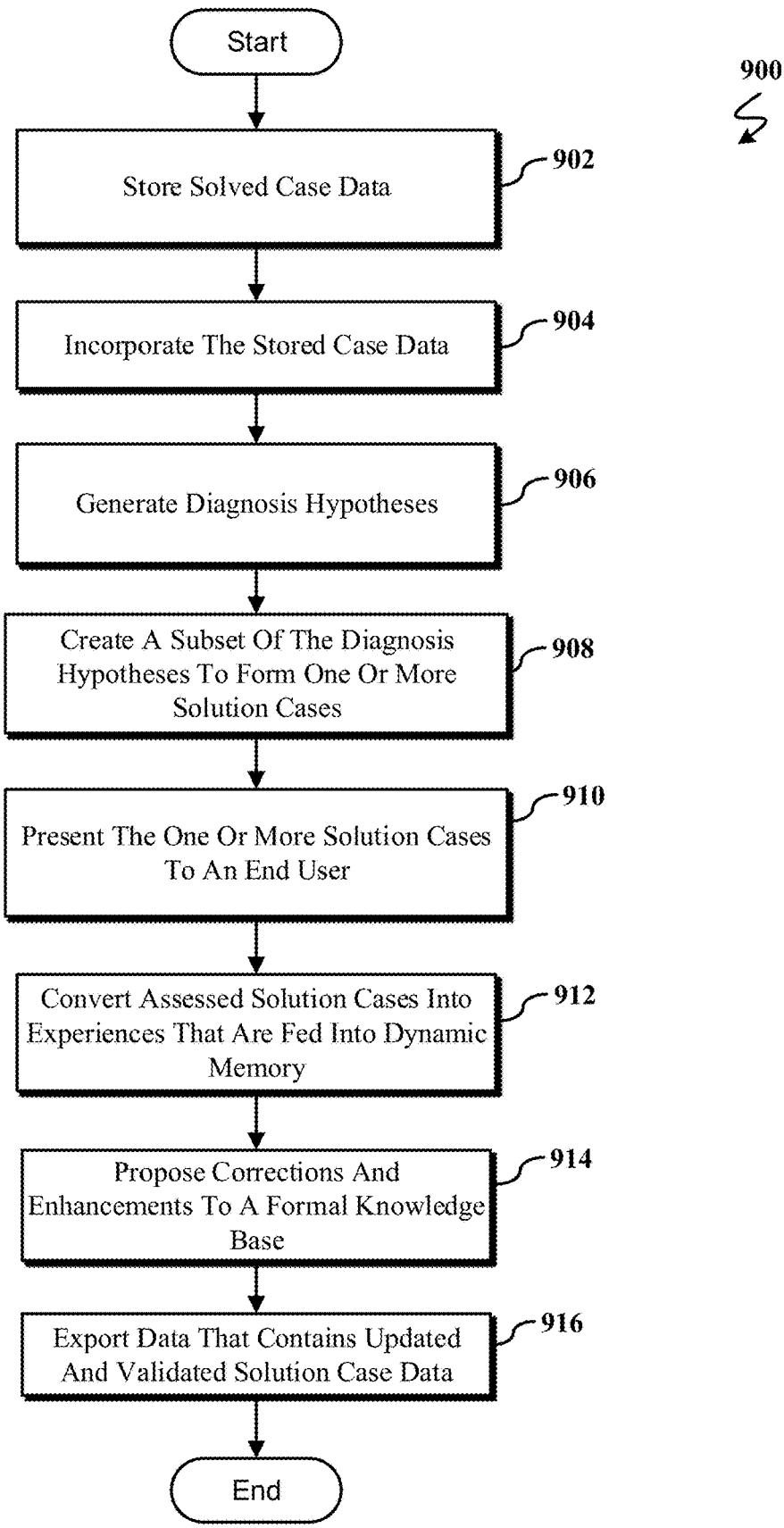
FIG. 9 illustrates an operational flowchart illustrating format exportation to a medical artificial intelligence analytics application performed by a disease identifier program according to at least one embodiment.

Referring now to FIG. 9, depicted is an operational flowchart illustrating an exemplary format exportation process 900 according to at least one embodiment. The process 900 may be executed by a processor or computer system (e.g., the disease identifier program 110a and 110b shown in FIG. 1). At 902, the disease identifier program 110a and 110b stores solved diagnosis case data utilizing a redundant discrimination net as a dynamic memory. The redundant discrimination net is discussed in more detail with reference to FIG. 7B. The solved diagnosis case data may be in the form of an electronic document inputted by the subject matter expert 204. The electronic document may have been a medical journal or a medical electronic textbook. The solved diagnosis case data may have been an electronic document from the internet ingested by the natural language processor accessed by utilizing a web crawling application designed to locate medical data on the Internet.

At 904, the disease identifier program 110a and 110b incorporates the stored solved diagnosis case data to form scientific descriptions within the formal knowledge base 248 and the empirical knowledge base 250. The descriptions and heuristics may include ailments, disorders, and diseases. The incorporation may be accomplished by utilizing automated reasoning as explained with reference to FIG. 2. At 906, the disease identifier program 110a and 110b generates at least one diagnosis hypothesis using the initial symptom description, the dynamic memory, the formal knowledge base 248, and the empirical knowledge base 250. The disease identifier program 110a and 110b may compare the initial symptom description that was transformed into data structures at 804 to the data structures stored in the dynamic memory, the formal knowledge base 248, and the empirical knowledge base 250 in a substantially similar way as described in operation 806.

At 908, the disease identifier program 110a and 110b creates a subset of the diagnosis hypotheses to form one or more solution cases. The solution cases may be substantially similar to the diagnosis description as explained with reference to FIG. 8, at 814 and 816. At 910, the disease identifier program 110a and 110b presents the one or more solution cases to the end user. The presentation to the end user may be accomplished in a substantially similar was as was performed at 812 or 814. The disease identifier program 110 a, b may present the solution case(s) to a subject matter expert. The disease identifier program 110a, b may then receive a response from the subject matter expert and identify, based on the response, a diagnosis success or a diagnosis failure.

At 912, the disease identifier program 110a, b converts assessed solution cases into experiences that are fed into the dynamic memory; a self-organizing process incorporates new knowledge as a result and improves performance in future diagnostic case sessions, as discussed with reference to FIG. 2. All retrieved cases from the case memory 252, the formal knowledge base 248, and the empirical knowledge base 250 may constitute solution cases. All solution cases may be analyzed and weighted, and redundancies may be removed. The resulting solution cases with the highest weights may be the most likely viable solutions cases. A solution case may be positive, that is, a solution case that has the probability of being successful, or it may be negative, meaning that the system could not find potentially successful cases, but offers cases that the disease diagnosing module 222 determines may not be successful alternatives and thus not worth pursuing further. The disease diagnosing module 222 may propose the selected solution case to the patient 202. The disease diagnosing module 222 may create new cases that may utilized when creating a new diagnosis description, which may be adaptations of the old, retrieved cases with the entire "solution path," that are search paths ending in a particular solution, produced by the initial problem description plus all the process steps. In some embodiments, only experiences that strictly have new information to the case memory 252 are considered.

These generated experiences may be stored in generated experiences 254, along with the solution path, and may be verified by the subject matter expert 204 or retrieved by the analytics system administrator 206 (e.g., an artificial intelligence analytics application). These experiences are ready for expert validation (e.g., the subject matter expert 204) before being incorporated by the learning module 234 to the case memory 252 as new solution cases. A case may be considered solved when the disease diagnosing module 222 provides the patient 202 with a disease based on the initial symptom description. The learning module 234 may create experiences, adapt information from past cases to new experiences, and store experiences in the database 114, formal knowledge base 248, or empirical knowledge base 250, for the subject matter expert 204 to determine whether the created experience is valid.

At 914, the disease identifier program 110 a, b proposes corrections and enhancements to the formal knowledge base 248 by analyzing the new knowledge incorporated against existing scientific descriptions and heuristics, as discussed with reference to FIG. 2. The medical knowledge base maintaining module 226 may keep the empirical knowledge base 250 up to date with the latest scientific and empirical data inputted by the subject matter expert 204, or ingested automatically by the medical knowledge base maintaining module 226 (e.g., from medical websites, scientific papers, published studies, etc.). The subject matter expert 204 may select either the empirical knowledge base 250 or the formal knowledge base 248 to analyze. The medical knowledge maintaining module 226 may then present the subject matter expert 204 with the selected knowledge base (i.e., the empirical knowledge base 250 or the formal knowledge base 248). The subject matter expert 204 (or the medical knowledge base maintaining module 226 itself) may then update diseases, symptoms, symptom synonyms, and heuristics within the empirical knowledge base 250 or the formal knowledge base 248, as appropriate, by adding new data, or modifying and deleting existing data. The subject matter expert 204 may signal the system to save all updated data. The medical knowledge maintaining module 226 may then save the data to the database 114, the empirical knowledge base 250, or the formal knowledge base 248.

At 916, the disease identifier program 110a, b exports data containing updated and validated solution case data in predetermined formats consumed by the analytics system administrator 206 (e.g., the medical artificial intelligence analytics application), as discussed with reference to FIG. 2. In some embodiments, the analytics system administrator 206 may be an automated user (e.g., a medical artificial intelligence analytics application) that may request solved case data stored in memory (e.g., database 114) for analysis and research. Case data providing module 228 may provide solved case data as requested by an analytics system administrator 206. The data explorer module 236 may follow the search paths in an effort to retrieve a set of relevant cases from the database 114 or case memory 252 using the initial symptom description as a search basis. The analytics system administrator 206 may request a data subset from the case data providing module 228 that has cases that satisfy a given set of parameters. For example, the cases may include cancer patients aged 24-50 years old or patients with diabetes living within a particular city. The analytics system administrator 206 may also request the data subset be in a particular type of file (e.g., .pdf, .doc, .exe, etc.), the data to be compressed, the data to be written in a certain programming language (e.g., C+, Java, etc.), the data being presented with a particular schema, or the data to be translated to a different format (e.g., audio, text, or video). The case data providing module 228 may transmit the requested data subset to the data explorer module 236. The data explorer module 236 may search for and then retrieve case data from the database 114. The retrieved data is provided in the format requested by the analytics system administrator 206. The case data providing module 228 may send the requested data to the analytics system administrator 206 in the certain type of file as requested by the analytics system administrator 206. Once the disease identifier program 110a, b exports data containing updated and validated solution case data in predetermined formats consumed by the analytics system administrator 206, the exportation process 900 may terminate.

Figure 10:
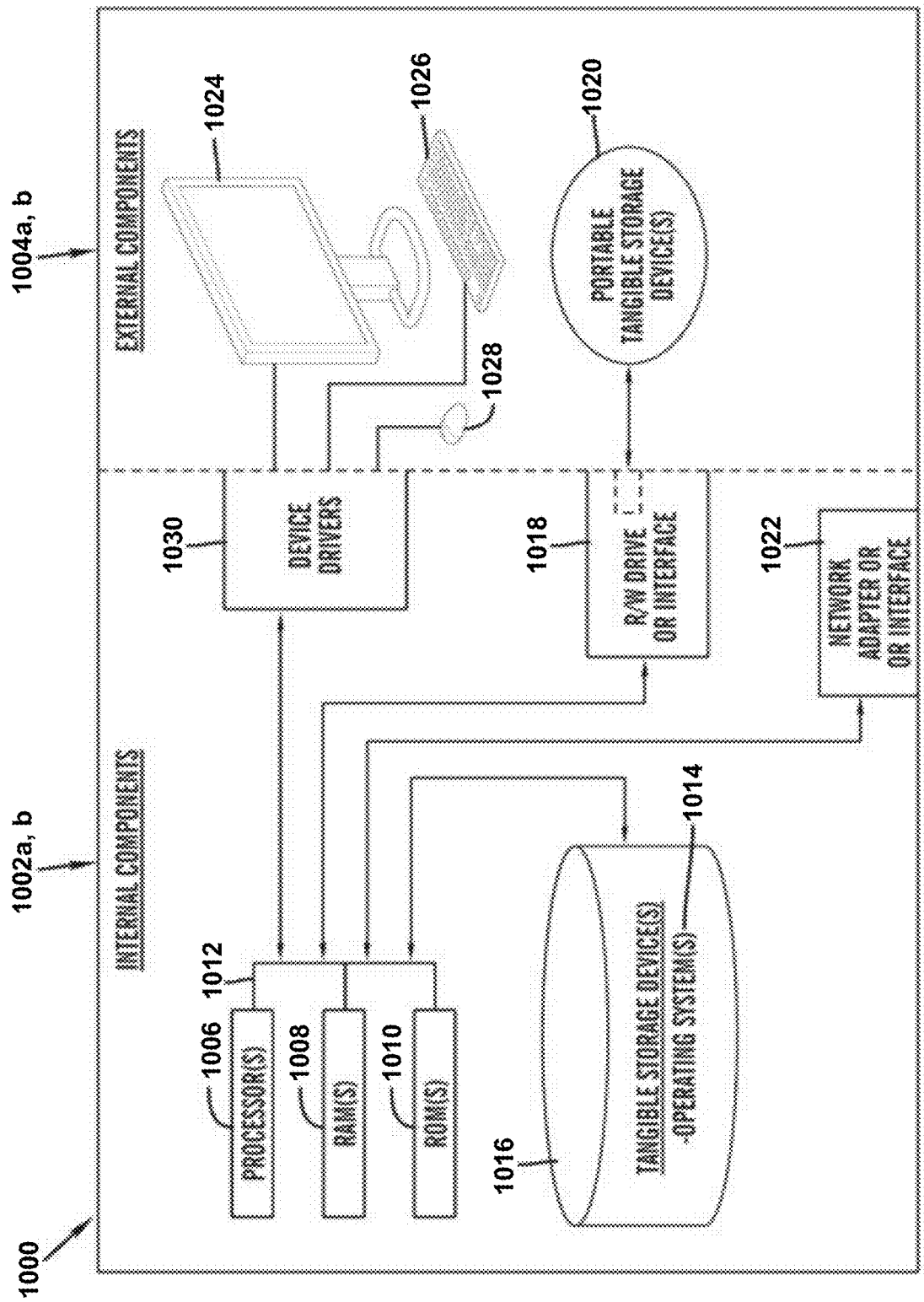
FIG. 10 is a block diagram of internal and external components of computers and servers depicted in FIG. 1 according to at least one embodiment.

FIG. 10 is a block diagram 1000 of internal and external components of computers depicted in FIG. 1 in accordance with an illustrative embodiment of the present invention. It should be appreciated that FIG. 10 provides only an illustration of one implementation and does not imply any limitations with regard to the environments in which different embodiments may be implemented. Many modifications to the depicted environments may be made based on design and implementation requirements.

Data processing system 1002a, b, and 1004, b is representative of any electronic device capable of executing machine-readable program instructions. Data processing system 1002a, b, and 1004, b may be representative of a smart phone, a computer system, PDA, or other electronic devices. Examples of computing systems, environments, and/or configurations that may represented by data processing system 1002a, b, and, 1004 a, b include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) may include respective sets of internal components 1002 a, b and external components 1004 a, b illustrated in FIG. 10. Each of the sets of internal components 1002 a, b includes one or more processors 1006, one or more computer-readable RAMs 1008 and one or more computer-readable ROMs 1010 on one or more buses 1012, and one or more operating systems 1014 and one or more computer-readable tangible storage devices 1016. The one or more operating systems 1014 and the software program 108 (FIG. 1) and the disease diagnosis program 110a (FIG. 1) in client computer 102 (FIG. 1) and the disease diagnosis program 110b (FIG. 1) in network server 112 (FIG. 1), may be stored on one or more computer-readable tangible storage devices 1016 for execution by one or more processors 1006 via one or more RAMs 1008 (which typically include cache memory). In the embodiment illustrated in FIG. 10, each of the computer-readable tangible storage devices 1016 is a magnetic disk storage device of an internal hard drive. Alternatively, each of the computer-readable tangible storage devices 1016 is a semiconductor storage device such as ROM 1010, EPROM, flash memory or any other computer-readable tangible storage device that can store a computer program and digital information.

Each set of internal components 1002 a, b also includes a R/W drive or interface 1018 to read from and write to one or more portable computer-readable tangible storage devices 1020 such as a CD-ROM, DVD, memory stick, magnetic tape, magnetic disk, optical disk or semiconductor storage device. A software program, such as the software program 108 (FIG. 1) and the disease diagnosis program 110a and 110b (FIG. 1) can be stored on one or more of the respective portable computer-readable tangible storage devices 1020, read via the respective R/W drive or interface 1018 and loaded into the respective hard drive 1016.

Each set of internal components 1002 a, b may also include network adapters (or switch port cards) or interfaces 1022 such as a TCP/IP adapter cards, wireless wi-fi interface cards, or 3G or 4G wireless interface cards or other wired or wireless communication links. The software program 108 (FIG. 1) and the disease diagnosis program 110a (FIG. 1) in client computer 102 (FIG. 1) and the disease diagnosis program 110b (FIG. 1) in network server computer 112 (FIG. 1) can be downloaded from an external computer (e.g., server) via a network (for example, the Internet, a local area network or other, wide area network) and respective network adapters or interfaces 1022. From the network adapters (or switch port adaptors) or interfaces 1022, the software program 108 (FIG. 1) and the disease diagnosis program 110a (FIG. 1) in client computer 102 (FIG. 1) and the disease diagnosis program 110b (FIG. 1) in network server computer 112 (FIG. 1) are loaded into the respective hard drive 1016. The network may comprise copper wires, optical fibers, wireless transmission, routers, firewalls, switches, gateway computers, and/or edge servers.

Each of the sets of external components 1004 a, b can include a computer display monitor 1024, a keyboard 1026, and a computer mouse 1028. External components 1004 a, b can also include touch screens, virtual keyboards, touch pads, pointing devices, and other human interface devices. Each of the sets of internal components 1002 a, b also includes device drivers 1030 to interface to computer display monitor 1024, keyboard 1026, and computer mouse 1028. The device drivers 1030, R/W drive or interface 1018 and network adapter or interface 1022 comprise hardware and software (stored in tangible storage device 1016 and/or ROM 1010).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 11:
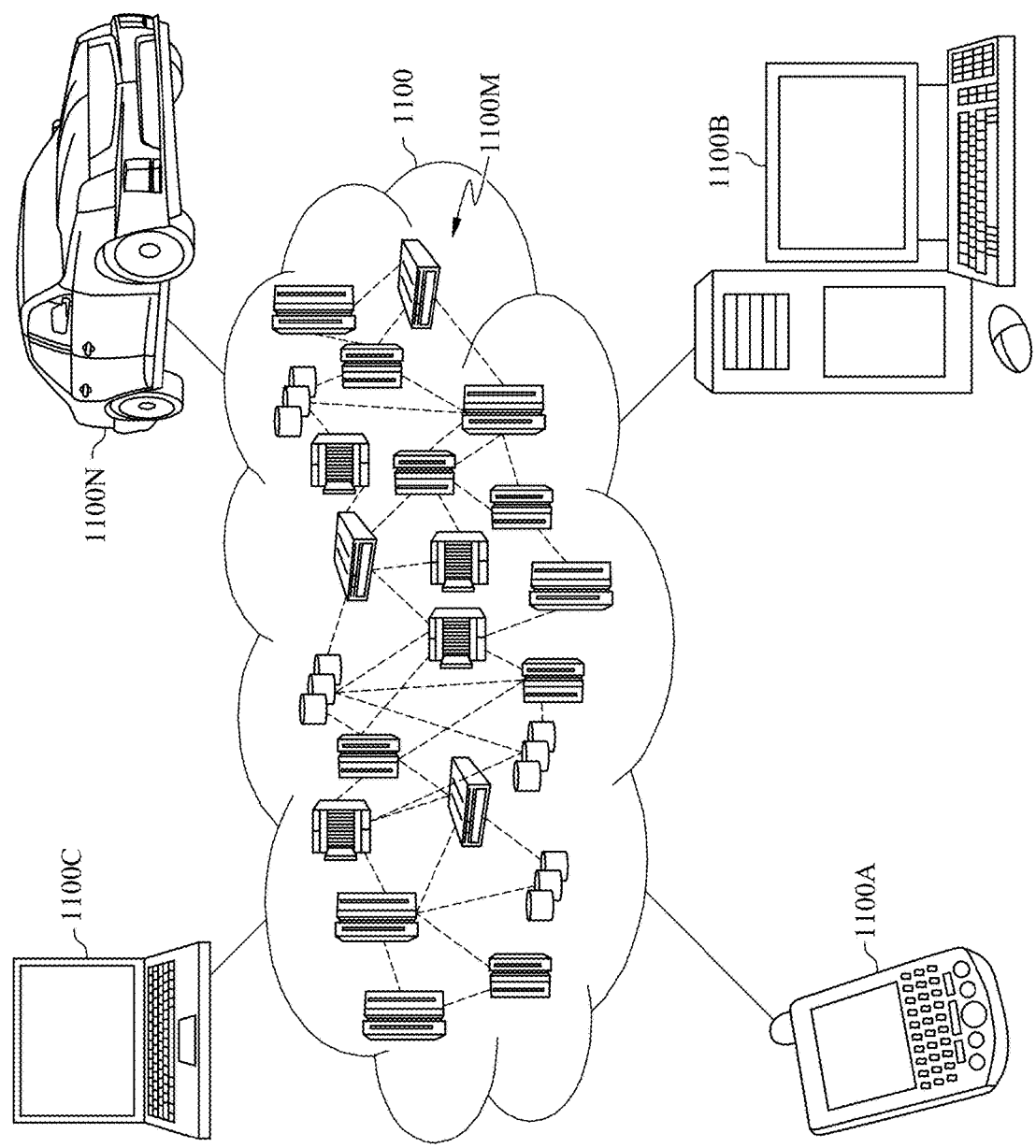
FIG. 11 is a block diagram of an illustrative cloud computing environment including the networked computer environment depicted in FIG. 1, in accordance with an embodiment of the present disclosure.

Referring now to FIG. 11, illustrative cloud computing environment 1100 is depicted. As shown, cloud computing environment 1100 comprises one or more cloud computing nodes 1100M (e.g., network computing environment 100) with which local computing devices (e.g., computer 102) used by cloud consumers, such as, for example, personal digital assistant (PDA) or cellular telephone 1100A, desktop computer 1100B, laptop computer 1100C, and/or automobile computer system 1100N may communicate. Nodes 1100M may communicate with one another. They may be grouped (not shown) physically or virtually, in one or more networks, such as Private, Community, Public, or Hybrid clouds as described hereinabove, or a combination thereof. This allows cloud computing environment 1100 to offer infrastructure, platforms and/or software as services for which a cloud consumer does not need to maintain resources on a local computing device. It is understood that the types of computing devices 1100A-N shown in FIG. 11 are intended to be illustrative only and that computing nodes 1100M and cloud computing environment 1100 can communicate with any type of computerized device over any type of network and/or network addressable connection (e.g., using a web browser).

Figure 12:
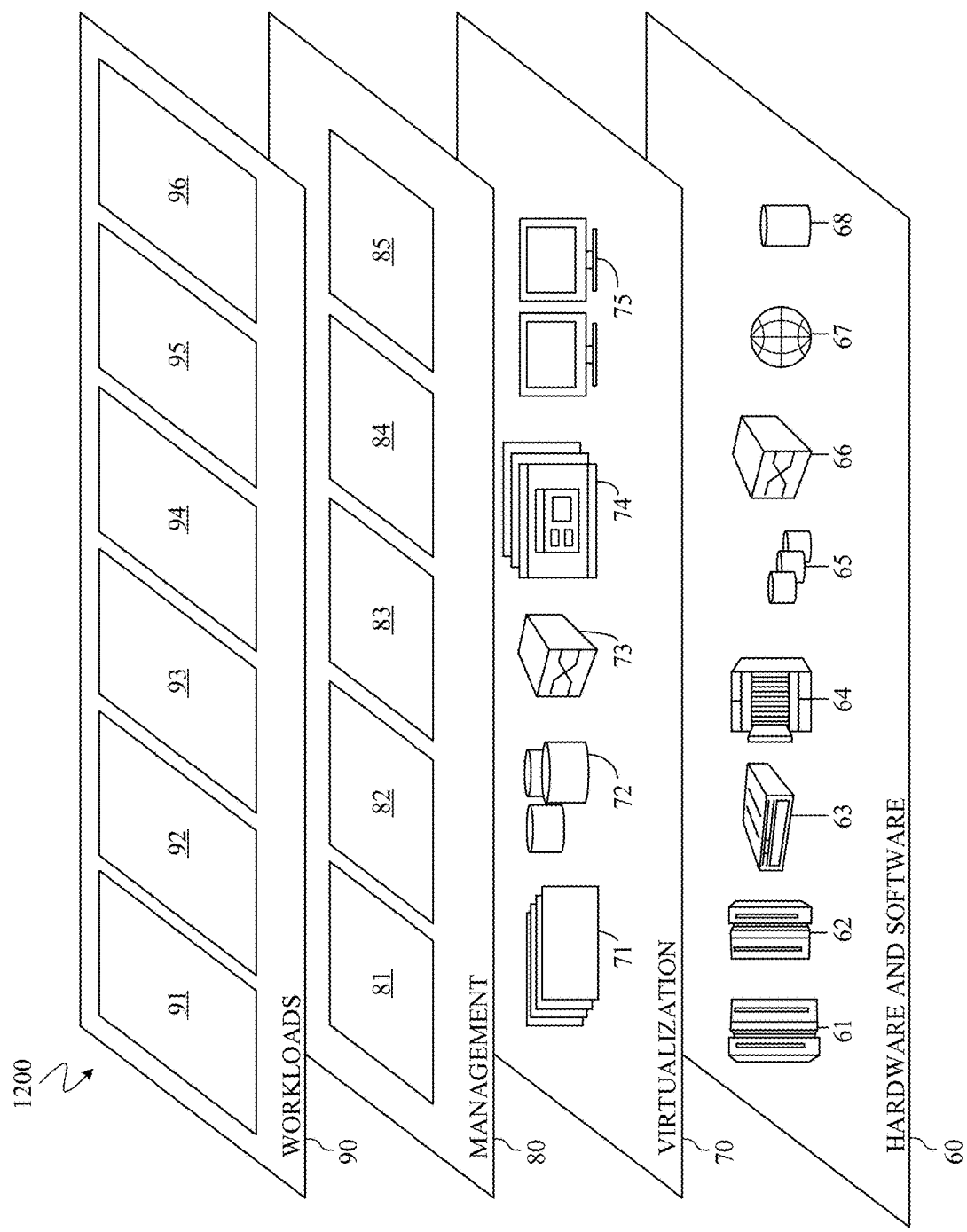
FIG. 12 is a block diagram of functional layers of the illustrative cloud computing environment of FIG. 11, in accordance with at least one embodiment of the present disclosure.

Referring now to FIG. 12, a set of functional abstraction layers 1200 provided by cloud computing environment 1100 (FIG. 11) is shown. It should be understood in advance that the components, layers, and functions shown in FIG. 12 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and disease diagnosis 96.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented process for generating ailment, disorder, and disease diagnostic data for consumption by a medical artificial intelligence analytics application, the computer-implemented process comprising:
   storing previously solved diagnosis case data utilizing a redundant discrimination net as a dynamic memory, wherein the redundant discrimination net includes multiple pathways for nodes including an index value pathway and a norm pathway;
   incorporating the stored diagnosis case data to form scientific descriptions within a medical knowledge base and heuristics within an empirical knowledge base;
   generating diagnosis hypotheses using an initial symptom description, the dynamic memory, and the medical knowledge base, the initial symptom description being received from an end user;
   creating a subset of the diagnosis hypotheses to form one or more solution cases;
   presenting the one or more solution cases to a subject matter expert;
   identifying, based on a response received from the subject matter expert, a diagnosis of the medical expert measurable by a metric to form an assessed solution case;
   converting assessed solution case into experiences;
   inputting the experiences into the dynamic memory; and
   transmitting data containing the assessed solution case to a medical artificial intelligence analytics application.

2. The method of claim 1, wherein the transmitted data contains updated and validated solution case data, the method further comprising:
   incorporating, using a self-organizing process, knowledge received from the assessed solution case against existing scientific descriptions and heuristics;
   proposing corrections and enhancements to the medical knowledge base by analyzing the new knowledge incorporated against existing scientific descriptions and heuristics; and
   generating the updated and validated solution case data.

3. The method of claim 2, wherein the transmitting the data to the medical artificial intelligence analytics application includes:
   receiving, from the medical artificial intelligence analytics application, a request to extract data and a corresponding file type for the one or more cases;
   determining a data format used by the medical artificial intelligence analytics applications;
   transforming the updated and validated solution case data into the data format used by the medical artificial intelligence analytics applications in response to the received request; and
   generating a file having the requested data and corresponding file type, wherein the file includes the transformed solution case data.

4. The method of claim 1, wherein the generating diagnosis hypotheses comprises:
   receiving an initial symptom description from the end user, wherein the initial symptom description comprises at least one of text, audio, or a video format;
   transforming, utilizing natural language processing, at least one of text, audio, or a video format into data structures; and
   comparing the data structures to similar data structures stored in case memory.

5. The method of claim 4, wherein the presented one or more solution cases are newly generated solution cases, the method further comprising:
   determining, that a quantity of descriptive elements in the transformed data structures to retrieve previously solved diagnosis case data, do not satisfy a diagnosis threshold; and
   generating one or more new solution cases in response to determining that the quantity does not satisfy the diagnosis threshold.

6. The method of claim 4, further comprising:
   determining, based on a numerical representation of the similarity between the data structures form an initial symptom description and data structures of a previous diagnosis, that the data structures do not satisfy an initial symptom description threshold; and
   requesting, in the form of a questionnaire, more information from the end user to add to the initial symptom description based on available information stored in case memory in response to determining that the data structures do not satisfy the initial symptom description threshold.

7. The method of claim 1, wherein the medical knowledge base includes one or more cases extracted from medical journals and medical dictionaries, the method further comprising:

transmitting, to the subject matter expert, the medical journals and medical dictionaries in the form of electronic documents.

8. A computer system for generating ailment, disorder, and disease diagnostic data for consumption by a medical artificial intelligence analytics application, the system comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

storing previously solved diagnosis case data utilizing a redundant discrimination net as a dynamic memory, wherein the redundant discrimination net includes multiple pathways for nodes including an index value pathway and a norm pathway;

incorporating the stored diagnosis case data to form scientific descriptions within a medical knowledge base and heuristics within an empirical knowledge base;

generating diagnosis hypotheses using an initial symptom description, the dynamic memory, and the medical knowledge base, the initial symptom description being received from an end user;

creating a subset of the diagnosis hypotheses to form one or more solution cases;

presenting the one or more solution cases to a subject matter expert;

identifying, based on a response received from the subject matter expert, a diagnosis of the medical expert measurable by a metric to form an assessed solution case;

converting assessed solution case into experiences;

inputting the experiences into the dynamic memory; and transmitting data containing the assessed solution case to a medical artificial intelligence analytics application.

9. The system of claim 8, wherein the transmitted data contains updated and validated solution case data, the method further comprising:

incorporating, using a self-organizing process, knowledge received from the assessed solution case against existing scientific descriptions and heuristics;

proposing corrections and enhancements to the medical knowledge base by analyzing the new knowledge incorporated against existing scientific descriptions and heuristics; and generating the updated and validated solution case data.

10. The system of claim 9, wherein the transmitting the data to the medical artificial intelligence analytics application includes:

receiving, from the medical artificial intelligence analytics application, a request to extract data and a corresponding file type for the one or more cases;

determining a data format used by the medical artificial intelligence analytics applications;

transforming the updated and validated solution case data into the data format used by the medical artificial intelligence analytics applications in response to the received request; and generating a file having the requested data and corresponding file type, wherein the file includes the transformed solution case data.

11. The system of claim 8, wherein the generating diagnosis hypotheses comprises:

receiving an initial symptom description from the end user, wherein the initial symptom description comprises at least one of text, audio, or a video format;

transforming, utilizing natural language processing, at least one of text, audio, or a video format into data structures; and comparing the data structures to similar data structures stored in case memory.

12. The system of claim 11, wherein the presented one or more solution cases are newly generated solution cases, the method further comprising:

determining, that a quantity of descriptive elements in the transformed data structures to retrieve previously solved diagnosis case data, do not satisfy a diagnosis threshold; and generating one or more new solution cases in response to determining that the quantity does not satisfy the diagnosis threshold.

13. The system of claim 11, further comprising:

determining, based on a numerical representation of the similarity between the data structures form an initial symptom description and data structures of a previous diagnosis, that the data structures do not satisfy an initial symptom description threshold; and requesting, in the form of a questionnaire, more information from the end user to add to the initial symptom description based on available information stored in case memory in response to determining that the data structures do not satisfy the initial symptom description threshold.

14. The system of claim 8, wherein the medical knowledge base includes one or more cases extracted from medical journals and medical dictionaries, the method further comprising:

transmitting, to the subject matter expert, the medical journals and medical dictionaries in the form of electronic documents.

15. A computer program product for generating ailment, disorder, and disease diagnostic data for consumption by a medical artificial intelligence analytics application, the computer program product comprising:

one or more computer-readable storage medium and program instructions stored on at least one of the one or more tangible storage medium, the program instructions executable by a processor, the program instructions comprising:

program instructions to store previously solved diagnosis case data utilizing a redundant discrimination net as a dynamic memory wherein the redundant discrimination net includes multiple pathways for nodes including an index value pathway and a norm pathway;

program instructions to incorporate the stored diagnosis case data to form scientific descriptions within a medical knowledge base and heuristics within an empirical knowledge base;

program instructions to generate diagnosis hypotheses using an initial symptom description, the dynamic memory, and the medical knowledge base, the initial symptom description being received from an end user;

program instructions to create a subset of the diagnosis hypotheses to form one or more solution cases;

program instructions to present the one or more solution cases to a subject matter expert;

program instructions to identify, based on a response received from the subject matter expert, a diagnosis of the medical expert measurable by a metric to form an assessed solution case;

program instructions to convert assessed solution case into experiences;

program instructions to input the experiences into the dynamic memory; and program instructions to transmit data containing the assessed solution case to a medical artificial intelligence analytics application.

16. The computer program product of claim 15, wherein the transmitted data contains updated and validated solution case data, the computer program product further comprising:

program instructions to incorporate, using a self-organizing process, knowledge received from the assessed solution case against existing scientific descriptions and heuristics;

program instructions to propose corrections and enhancements to the medical knowledge base by analyzing the new knowledge incorporated against existing scientific descriptions and heuristics; and program instructions to generate the updated and validated solution case data.

17. The computer program product of claim 16, wherein the transmitting the data to the medical artificial intelligence analytics application includes:

program instructions to receive, from the medical artificial intelligence analytics application, a request to extract data and a corresponding file type for the one or more cases;

program instructions to determine a data format used by the medical artificial intelligence analytics applications;

program instructions to transform the updated and validated solution case data into the data format used by the medical artificial intelligence analytics applications in response to the received request; and program instructions to generate a file having the requested data and corresponding file type, wherein the file includes the transformed solution case data.

18. The computer program product of claim 15, wherein the generating diagnosis hypotheses comprises:

program instructions to receive an initial symptom description from the end user, wherein the initial symptom description comprises at least one of text, audio, or a video format;

program instructions to transform, utilizing natural language processing, at least one of text, audio, or a video format into data structures; and program instructions to compare the data structures to similar data structures stored in case memory.

19. The computer program product of claim 18, wherein the presented one or more solution cases are newly generated solution cases, the computer program product further comprising:

program instructions to determine, that a quantity of descriptive elements in the transformed data structures to retrieve previously solved diagnosis case data, do not satisfy a diagnosis threshold; and program instructions to generate one or more new solution cases in response to determining that the quantity does not satisfy the diagnosis threshold.

20. The computer program product of claim 18, further comprising:

program instructions to determine, based on a numerical representation of the similarity between the data structures form an initial symptom description and data structures of a previous diagnosis, that the data structures do not satisfy an initial symptom description threshold; and program instructions to request, in the form of a questionnaire, more information from the end user to add to the initial symptom description based on available information stored in case memory in response to determining that the data structures do not satisfy the initial symptom description threshold.

* * * * *